US012706221B2

(12) United States Patent
Decker et al.

(10) Patent No.: US 12,706,221 B2
(45) Date of Patent: Aug. 11, 2026

(54) CALCULATING VIRAL TRANSFER RISK AND REDUCING EXPOSURE THROUGH OCCUPANCY OPTIMIZATION

(71) Applicant: Optum, Inc., Minnetonka, MN (US)

(72) Inventors: Brian Decker, Bonifacius, MN (US); Hadi D. Halim, Kendall Park, NJ (US); Gregory J. Boss, Saginaw, MI (US); Ranjan Prasad, Eden Prairie, MN (US)

(73) Assignee: Optum, Inc., Minnetonka, MN (US)

( * ) Notice: Subject to any disclaimer, the term of this patent is extended or adjusted under 35 U.S.C. 154(b) by 395 days.

(21) Appl. No.: 17/466,914

(22) Filed: Sep. 3, 2021

(65) Prior Publication Data

US 2022/0270764 A1 Aug. 25, 2022

Related U.S. Application Data

(60) Provisional application No. 63/200,186, filed on Feb. 19, 2021.

(51) Int. Cl.
*G16H 50/80* (2018.01)
*G05B 19/042* (2006.01)
(Continued)

(52) U.S. Cl.
CPC ........... *G16H 50/80* (2018.01); *G05B 19/042* (2013.01); *G06Q 10/02* (2013.01); *G16H 10/60* (2018.01);
(Continued)

(58) Field of Classification Search
CPC .......... G05B 2219/2614; G05B 19/042; H04L 9/0866; G16H 50/70; G16H 50/80; G16H 10/60; G16H 50/30; G06Q 10/02
See application file for complete search history.

(56) References Cited

U.S. PATENT DOCUMENTS 6,085,976 A 7/2000 Sehr
9,858,631 B2 1/2018 Farr et al.
(Continued)

FOREIGN PATENT DOCUMENTS

WO WO-2020018147 A1 * 1/2020 ............ G05B 15/02
WO 2022/015719 A1 1/2022

OTHER PUBLICATIONS

Peltoniemi. Evaluating Blockchain for the Governance of the Plasma Derivatives Supply Chain: How Distributed Ledger Technology Can Mitigate Plasma Supply Chain Risks. Blockchain in Healthcare Today. 2019. (Year: 2019).*
(Continued)

*Primary Examiner* — Christopher L Gilligan
*Assistant Examiner* — Tristan Isaac Evans
(74) *Attorney, Agent, or Firm* — ALSTON & BIRD LLP

(57) ABSTRACT

Embodiments herein relate to viral transfer risk management. In example embodiments, an apparatus is configured to retrieve a first user identifier associated with a first client computing entity. The apparatus is further configured to determine, based at least in part on a first transfer risk score associated with the first user identifier, a first transfer risk score grouping for the first user identifier. The apparatus is further configured to, based at least in part on the first transfer risk score grouping and physical space parameters associated with a physical space identifier, allocate a first physical space assignment within a physical space associated with the physical space identifier to the first user identifier associated with the first client computing entity.

23 Claims, 19 Drawing Sheets

(51) Int. Cl.

| | |
|---|---|
| ***G06Q 10/02*** | (2012.01) |
| ***G16H 10/60*** | (2018.01) |
| ***G16H 50/30*** | (2018.01) |
| ***G16H 50/70*** | (2018.01) |
| ***H04L 9/08*** | (2006.01) |

(52) U.S. Cl.

CPC ............. *G16H 50/30* (2018.01); *G16H 50/70* (2018.01); *H04L 9/0866* (2013.01); *G05B 2219/2614* (2013.01)

(56) References Cited

U.S. PATENT DOCUMENTS

| | | | | |
|---|---|---|---|---|
| 11,011,277 | B1 * | 5/2021 | Kelly | G16H 40/67 |
| 11,013,472 | B1 * | 5/2021 | Frieder | A61B 5/1112 |
| 11,356,810 | B1 * | 6/2022 | Akpinar | G16H 50/80 |
| 11,378,299 | B2 * | 7/2022 | Schoch | F24F 11/48 |
| 11,393,568 | B2 * | 7/2022 | Blackley | H04L 9/0861 |
| 11,504,011 | B1 * | 11/2022 | Jain | G06N 5/04 |
| 12,164,272 | B2 * | 12/2024 | Rafiee | G06Q 10/06311 |
| 2003/0229452 | A1 | 12/2003 | Lewis et al. | |
| 2009/0281836 | A1 | 11/2009 | Velarde | |
| 2011/0131055 | A1 | 6/2011 | Grady et al. | |
| 2013/0055692 | A1 | 3/2013 | Cecchi et al. | |
| 2015/0088545 | A1 | 3/2015 | Daub et al. | |
| 2016/0283666 | A1 | 9/2016 | Kutscher et al. | |
| 2017/0330295 | A1 | 11/2017 | Alden et al. | |
| 2020/0090089 | A1 * | 3/2020 | Aston | G06Q 10/0635 |
| 2020/0200416 | A1 * | 6/2020 | Granger | G16H 40/67 |
| 2020/0321088 | A1 | 10/2020 | Liege et al. | |
| 2020/0401954 | A1 * | 12/2020 | Koslu | G06Q 10/04 |
| 2021/0011444 | A1 * | 1/2021 | Risbeck | F24F 11/52 |
| 2021/0082583 | A1 | 3/2021 | Ehrlich et al. | |
| 2021/0357820 | A1 | 11/2021 | Weir et al. | |
| 2022/0011746 | A1 | 1/2022 | Jorgenson et al. | |
| 2022/0115137 | A1 * | 4/2022 | Goldstein | G16H 10/60 |
| 2022/0246304 | A1 * | 8/2022 | Shyu | G16H 40/20 |
| 2023/0243797 | A1 * | 8/2023 | Onghanseng | G08B 21/12<br>73/31.05 |

OTHER PUBLICATIONS

Sun, Chanjuan. The efficacy of social distance and ventilation effectiveness in preventing COVID-19 transmission. Sustainable Cities and Society. 2020. (Year: 2020).*

Choisy. Mathematical Modeling of Infectious Diseases Dynamics. Encyclopedia of Infectious Diseases: Modern Methodologies, by M.Tibayrenc Copyright © 2007 John Wiley & Sons, Inc. (Year: 2007).*

Lipinski. Review of Ventilation Strategies to Reduce the Risk of Disease Transmission in High Occupancy Buildings. International Journal of Thermofluids 7-8 (2020) 100045. (Year: 2020).*

Fernandez, N. Self-Correcting HVAC Controls Project Final Report. Prepared for the US Department of Energy under contract DE-AC05-76RL01830. Dec. 2009. (Year: 2009).*

Azimi, P. HAVC filtration for controlling infectious airborne disease transmission in indoor environments: predicting risk reductions and operational costs. Building and Environment 70 (2013) 150-160. (Year: 2013).*

Jelodar. Deep sentiment classification and topic discovery on novel coronavirus or COVID-19 online discussion: NLP using LSTM recurrent neural network approach. IEEE JBHI, vol. 24, No. 10, Oct. 2020. (Year: 2020).*

Hayashi M, Yanagi U, Azuma K, Kagi N, Ogata M, Morimoto S, et al. Measures against COVID-19 concerning Summer Indoor Environment in Japan. Jpn Archit Rev. 2020; 3: 423-434. https://doi.org/10.1002/2475-8876.12183 (Year: 2020).*

Zhang, J. (2020). Integrating IAQ control strategies to reduce the risk of asymptomatic SARS CoV-2 infections in classrooms and open plan offices. Science and Technology for the Built Environment, 26(8), 1013-1018. https://doi.org/10.1080/23744731.2020.1794499 (Year: 2020).*

Escombe AR, Oeser CC, Gilman RH, Navincopa M, Ticona E, et al. (2007) Natural Ventilation for the Prevention of Airborne Contagion. PLOS Medicine 4(2): e68. https://doi.org/10.1371/journal.pmed.0040068 (Year: 2007).*

Guo, Yong, et al. "Assessing and controlling infection risk with Wells-Riley model and spatial flow impact factor (SFIF)." Sustainable Cities and Society 67 (2021): 102719. (Year: 2021).*

"Coronavirus: New Facts about Infection Mechanisms—NHK Documentary," YouTube video dated Apr. 3, 2020, (3 pages), [Online], [Retrieved from the Internet Sep. 21, 2021] <URL: https://www.youtube.com/watch?app=desktop&v=H2azcn7MqOU>.

"Cough Source 4D Isometric," YouTube video dated Apr. 30, 2020, (1 page), [Online}, [Retrieved from the Internet Sep. 21, 2021] <URL: https://www.youtube.com/watch?app=desktop&v=_VSHxkyppFU&feature=emb_logo>.

"microCOVID Project," (online), (2 pages), [Retrieved from the Internet Sep. 21, 2021] <URL: https://www.microcovid.org/>.

Allen, Joseph. "Ventilation & Filtration: Prevent COVID 19 + Optimize Health (Air Purifiers, HEPA Filters)," YouTube video dated Jan. 16, 2021, (32 pages), [Online], [Retrieved from the Internet Sep. 21, 2021] <URL: https://www.youtube.com/watch?app=desktop&v=OQ6DhgwgtGw>.

Anekal, Smartha G. et al. "Dynamics of Virus Spread in the Presence of Fluid Flow," Integrative Biology, Aug. 27, 2009, vol. 1, pp. 664-671, DOI: 10.1039/b908197f.

Bartzokas, Nick et al. "Why Opening Windows Is a Key to Reopening Schools," New York Times, Feb. 26, 2021, (article, online), (41 pages), [Retrieved from the Internet Sep. 21, 2021] <URL: https://www.nytimes.com/interactive/2021/02/26/science/reopen-schools-safety-ventilation.html?smtyp=cur&smid=tw-nytimes>.

Polley, John C. et al. "On an Innovative Architecture for Digital Immunity Passports and Vaccination Certificates," arXiv preprint arXiv:2103.04142, Mar. 6, 2021, (7 pages).

Final Rejection Mailed on Apr. 4, 2024 for U.S. Appl. No. 17/466,894, 35 page(s).

NonFinal Office Action for U.S. Appl. No. 17/466,894, dated Sep. 18, 2023, (30 pages), United States Patent and Trademark Office, US.

* cited by examiner

500

502

503

501

| Time segments | Risk Score | Risk Ceiling Score |
|---|---|---|
| 5:00:00 PM | 19% | 20% |
| 5:30:00 PM | 53% | 60% |
| 6:00:00 PM | 49% | 50% |
| 6:30:00 PM | 56% | 60% |
| 7:00:00 PM | 28% | 30% |
| 7:30:00 PM | 19% | 20% |
| 8:00:00 PM | 49% | 50% |
| 8:30:00 PM | 30% | 30% |
| 9:00:00 PM | 4% | 10% |
| 9:30:00 PM | 38% | 40% |
| 10:00:00 PM | 35% | 40% |
| 10:30:00 PM | 24% | 30% |
| 11:00:00 PM | 16% | 20% |
| 11:30:00 PM | 11% | 20% |
| 12:00:00 AM | 21% | 30% |
| 12:30:00 AM | 7% | 10% |
| 1:00:00 AM | 28% | 30% |

| | Reservation based on Risk level | | | | | |
|---|---|---|---|---|---|---|
| | Yellow | Blue | Green | Red | Risk score | Risk score ceiling |
| 5:00:00 PM | 16 | 47 | 29 | 21 | 19% | 20% |
| 5:30:00 PM | 14 | 0 | 30 | 49 | 53% | 60% |
| 6:00:00 PM | 8 | 21 | 6 | 33 | 49% | 50% |
| 6:30:00 PM | 12 | 9 | 16 | 47 | 56% | 60% |
| 7:00:00 PM | 43 | 5 | 34 | 32 | 28% | 30% |
| 7:30:00 PM | 40 | 35 | 39 | 27 | 19% | 20% |
| 8:00:00 PM | 25 | 22 | 2 | 47 | 49% | 50% |
| 8:30:00 PM | 46 | 33 | 28 | 45 | 30% | 30% |
| 9:00:00 PM | 23 | 28 | 34 | 4 | 4% | 10% |
| 9:30:00 PM | 36 | 7 | 5 | 29 | 38% | 40% |
| 10:00:00 PM | 24 | 35 | 30 | 48 | 35% | 40% |
| 10:30:00 PM | 46 | 10 | 21 | 24 | 24% | 30% |
| 11:00:00 PM | 42 | 43 | 30 | 22 | 16% | 20% |
| 11:30:00 PM | 31 | 1 | 25 | 7 | 11% | 20% |
| 12:00:00 AM | 24 | 16 | 46 | 23 | 21% | 30% |
| 12:30:00 AM | 49 | 29 | 26 | 8 | 7% | 10% |
| 1:00:00 AM | 41 | 33 | 35 | 43 | 28% | 30% |

FIG. 13

1404: Retrieve a plurality of nearby user identifiers each associated with a different nearby client computing entity of a plurality of nearby client computing entities within a first proximity of the first client computing entity 1405: For each nearby user identifier of the plurality of nearby user identifiers, determine, based at least in part on a respective transfer risk score associated with the nearby user identifier, a respective transfer risk score grouping 1406: Detect a change in location associated with the first client computing entity, based at least in part on the physical space parameters, locations associated with the plurality of nearby client computing entities, and the respective transfer risk score groupings associated with the plurality of nearby user identifiers 1407: Transmit a collision potential notification to the first client computing entity

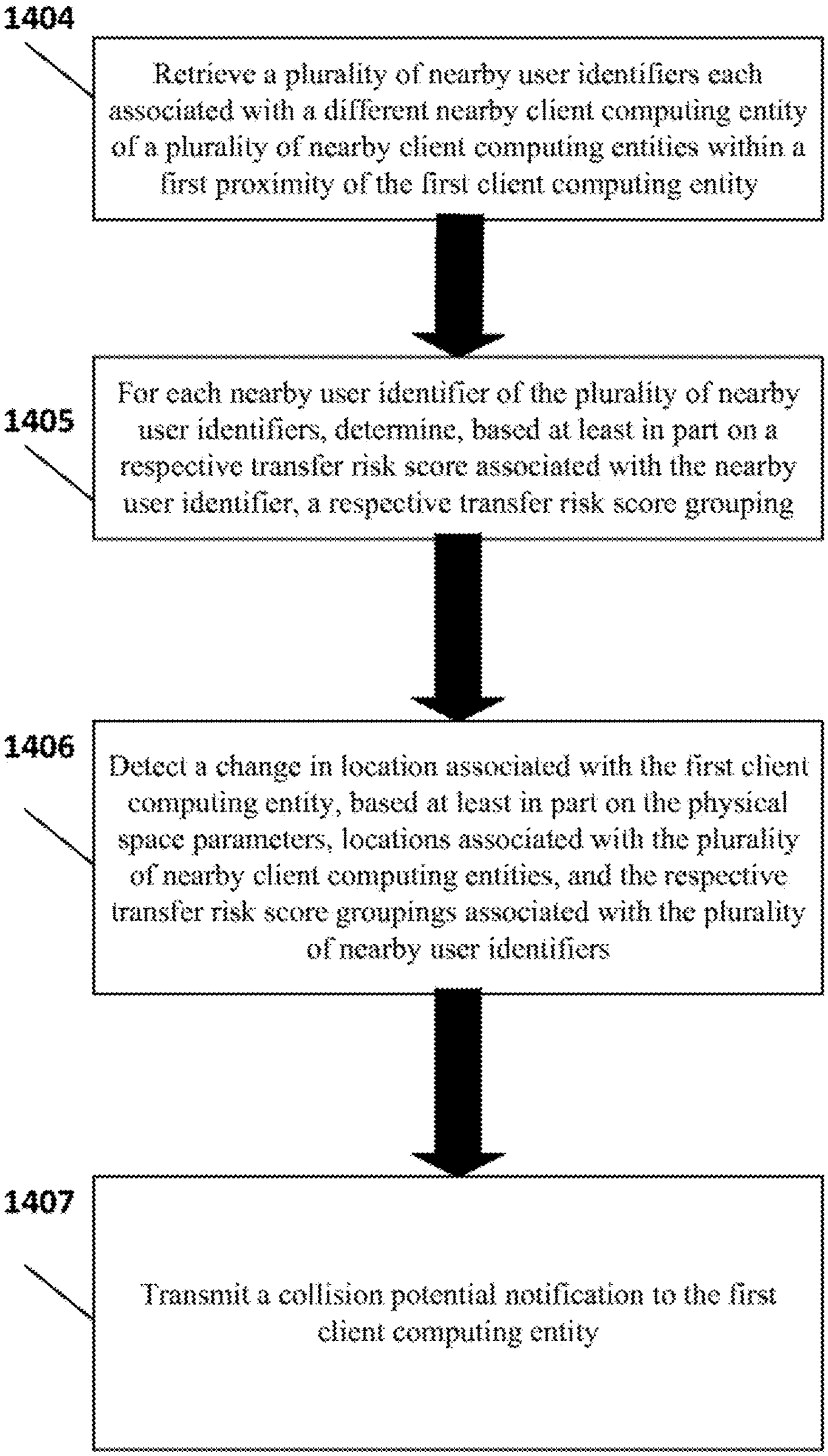

FIG. 14B

CALCULATING VIRAL TRANSFER RISK AND REDUCING EXPOSURE THROUGH OCCUPANCY OPTIMIZATION

CROSS-REFERENCE TO RELATED APPLICATIONS

The present application claims priority to U.S. Provisional Application Ser. No. 63/200,186, titled "CALCULATING VIRAL TRANSFER RISK AND REDUCING EXPOSURE THROUGH OCCUPANCY OPTIMIZATION," filed Feb. 19, 2021, the contents of which are incorporated herein by reference in their entirety.

BACKGROUND

Transmission of infectious diseases happens in many ways depending upon the virus or bacteria with which the infectious disease is associated. Viruses and bacteria can be associated with environmental sources, such as dry surfaces (e.g., railings, chairs, countertops, tables, armrests), wet surfaces, moist environments, and biofilms (e.g., faucets and sinks), dust or decaying debris (e.g., construction dust or wet materials from water leaks). Viruses and bacteria can be transmitted through contact (e.g., touching), sprays and splashes, inhalation, and injuries. Contact moves viruses and bacteria by touch; sprays and splashes occur when an infected person coughs or sneezes creating droplets which carry viruses or bacteria short distances (within approximately 6 feet). The droplets can land on a susceptible person's eyes, nose, or mouth and can cause infection. Inhalation occurs when virus or bacteria are aerosolized in tiny particles that survive on air currents over varying distances and time and reach a susceptible person. Airborne transmission can occur when an infected or infectious person coughs, talks, or sneezes virus or bacteria into the air or when virus or bacteria are aerosolized by equipment or by dust.

Congregating indoors during periods of high transmissibility, for example during a global pandemic (e.g., COVID-19), can contribute to the spread of disease if not carefully controlled. Through applied effort, ingenuity, and innovation, many problems associated with optimizing allocation of and adjusting parameters associated with physical spaces based at least in part on viral transmission risk have been solved by developing solutions that are included in embodiments of the present disclosure, many examples of which are described in detail herein.

BRIEF SUMMARY

Embodiments herein relate to viral transfer risk management. In example embodiments, an apparatus is configured to retrieve a first user identifier associated with a first client computing entity. The apparatus is further configured to determine, based at least in part on a first transfer risk score associated with the first user identifier, a first transfer risk score grouping for the first user identifier. The apparatus is further configured to, based at least in part on the first transfer risk score grouping and physical space parameters associated with a physical space identifier, allocate a first physical space assignment within a physical space associated with the physical space identifier to the first user identifier associated with the first client computing entity. In other example embodiments, an apparatus is configured to detect or receive a plurality of locations, each location associated with a different client computing entity of a plurality of client computing entities within a physical space associated with a physical space identifier. The apparatus is further configured to retrieve a plurality of user identifiers each associated with a different client computing entity of the plurality of client computing entities and, for each user identifier of the plurality of user identifiers, determine, based at least in part on a respective transfer risk score associated with the user identifier, a respective transfer risk score grouping. The apparatus is further configured to, based at least in part on respective transfer risk score groupings and physical space parameters associated with a physical space identifier, initiate one or more corrective actions.

BRIEF DESCRIPTION OF THE DRAWINGS

Figure 1:
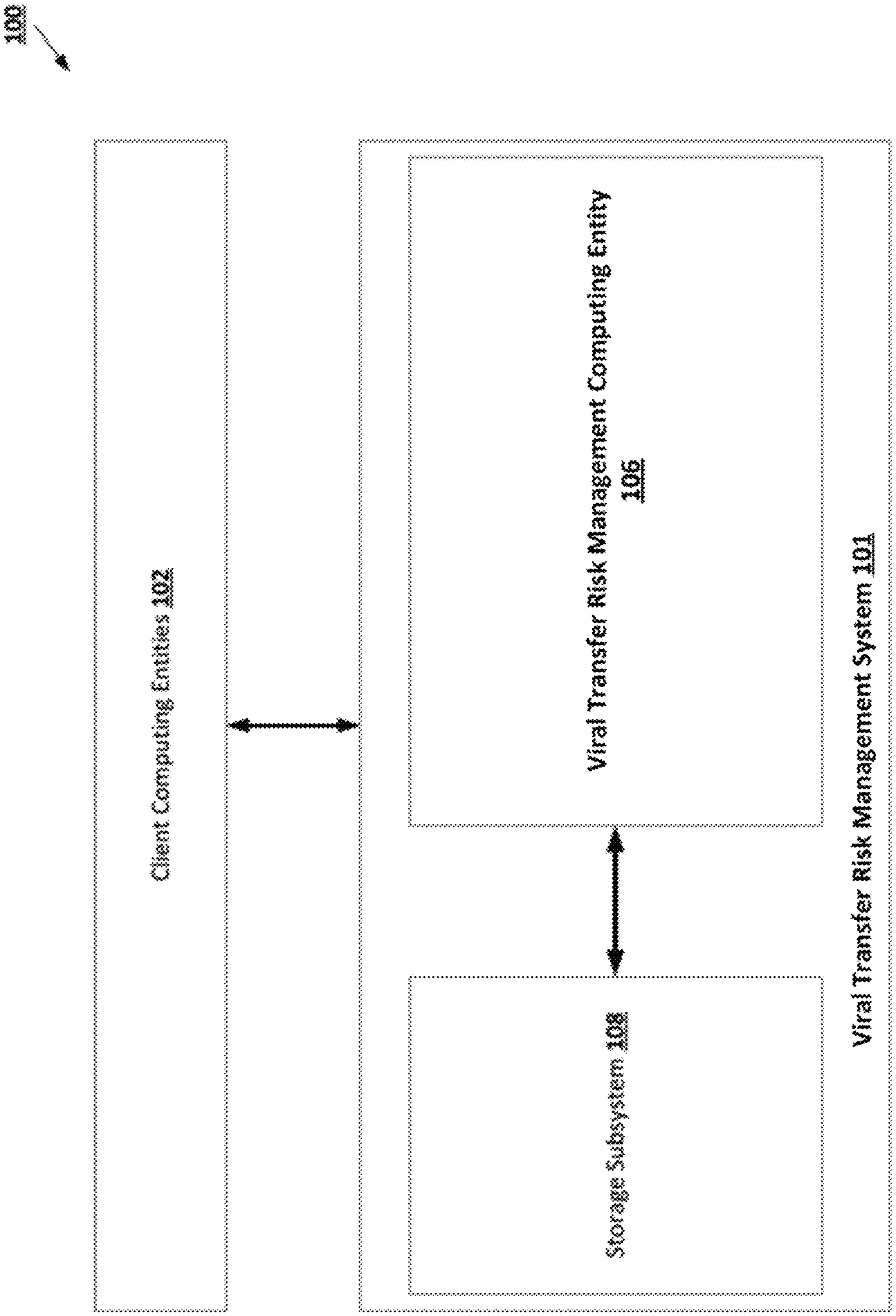

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
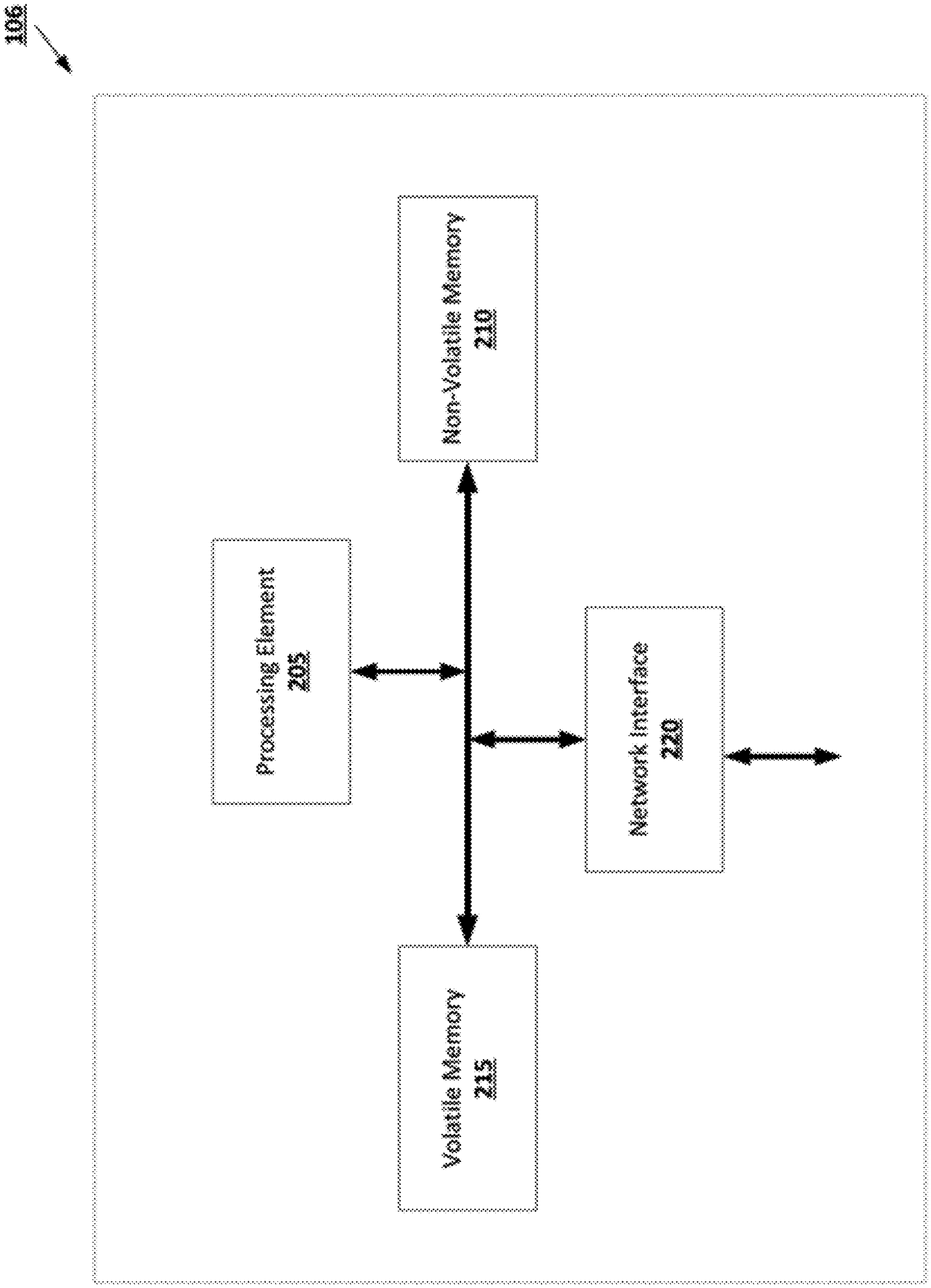

FIG. 2 provides an example viral transfer risk management computing entity in accordance with some embodiments discussed herein.

Figure 3:
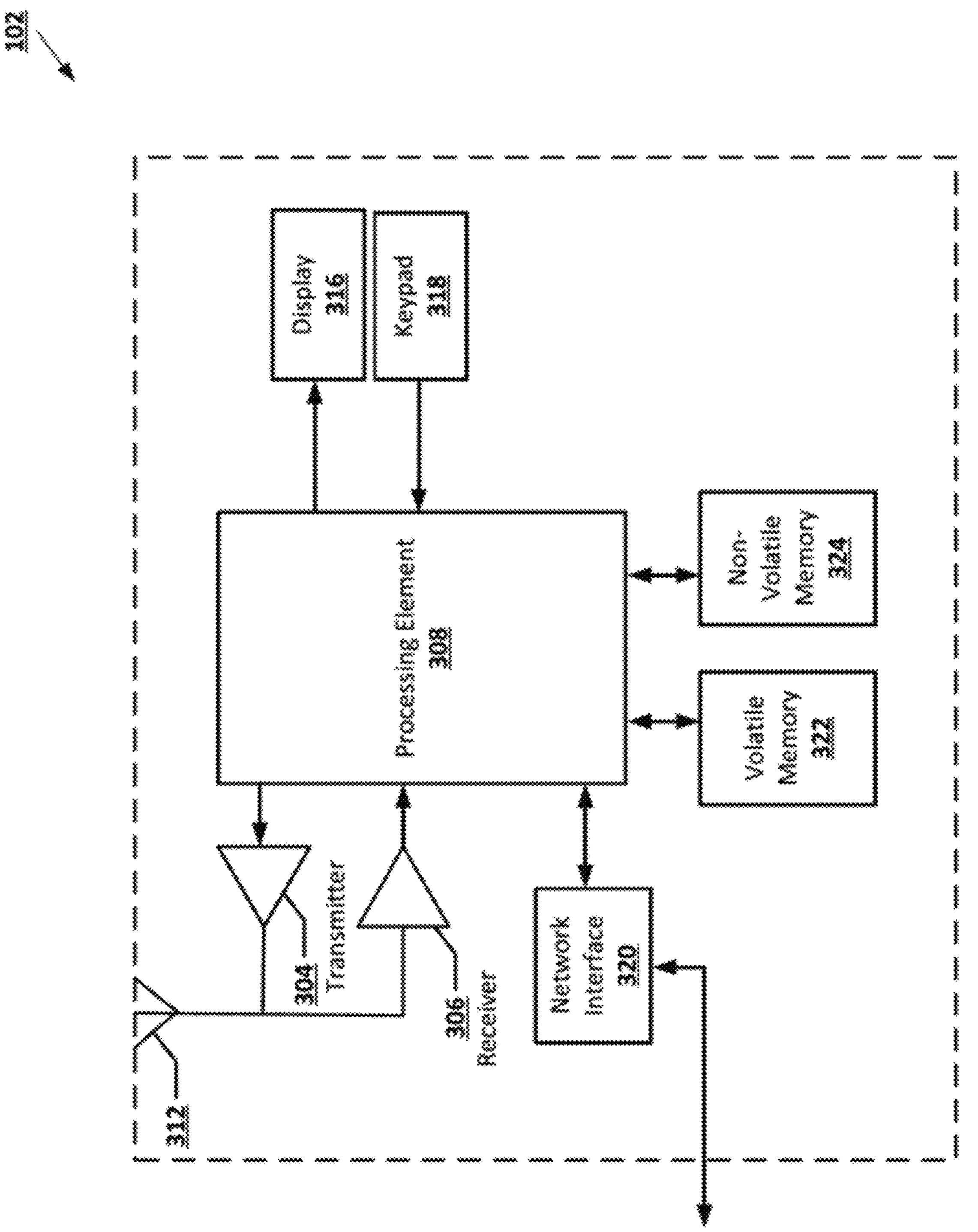

FIG. 3 provides an example client computing entity in accordance with some embodiments discussed herein.

Figure 4:
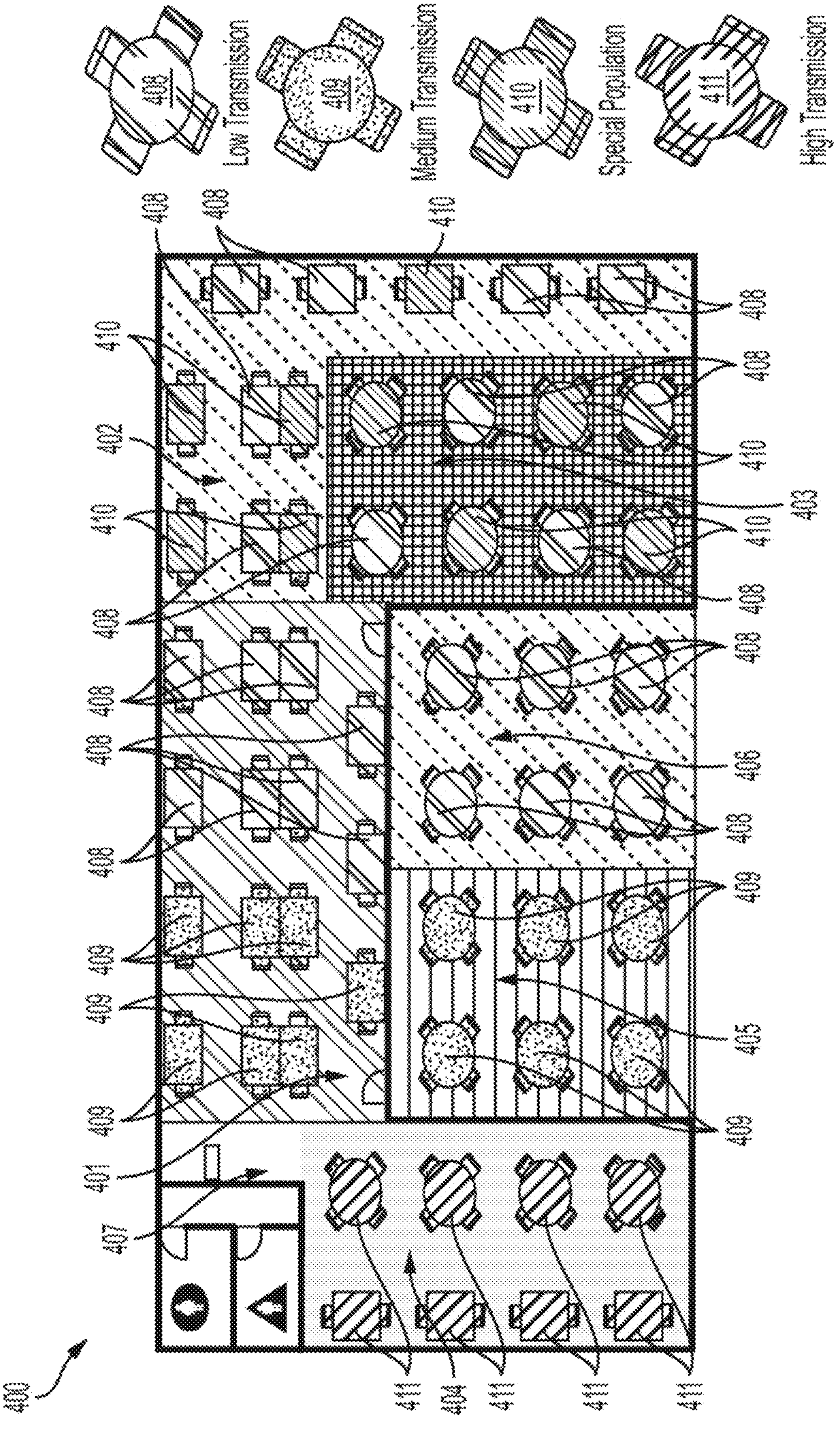

FIG. 4 depicts an example physical space allocation configuration in accordance with embodiments of the present disclosure.

FIG. 5 depicts an example physical space allocation schedule in accordance with embodiments of the present disclosure.

Figure 6:
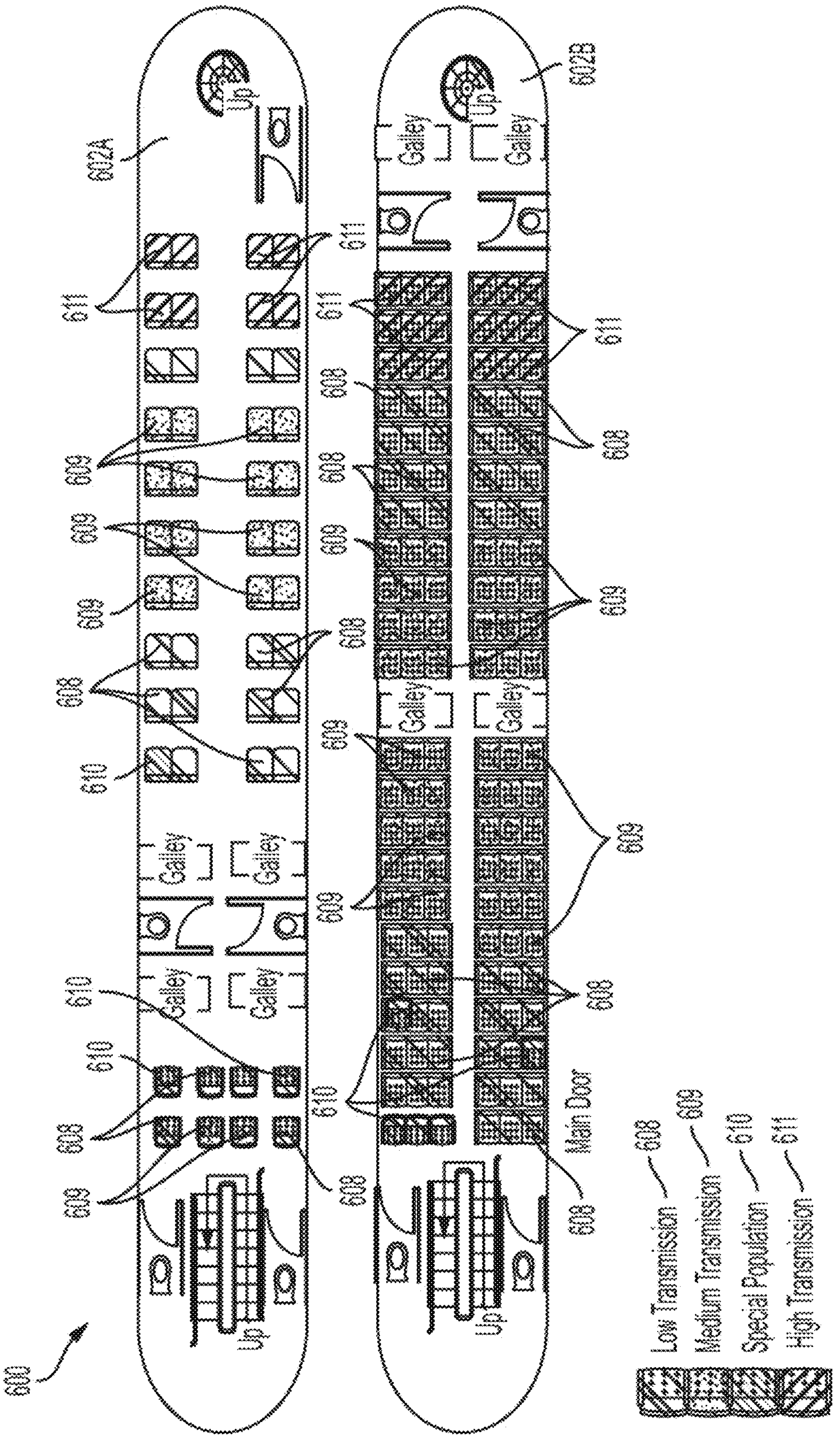

FIG. 6 depicts an example physical space allocation configuration in accordance with embodiments of the present disclosure.

Figure 7A:
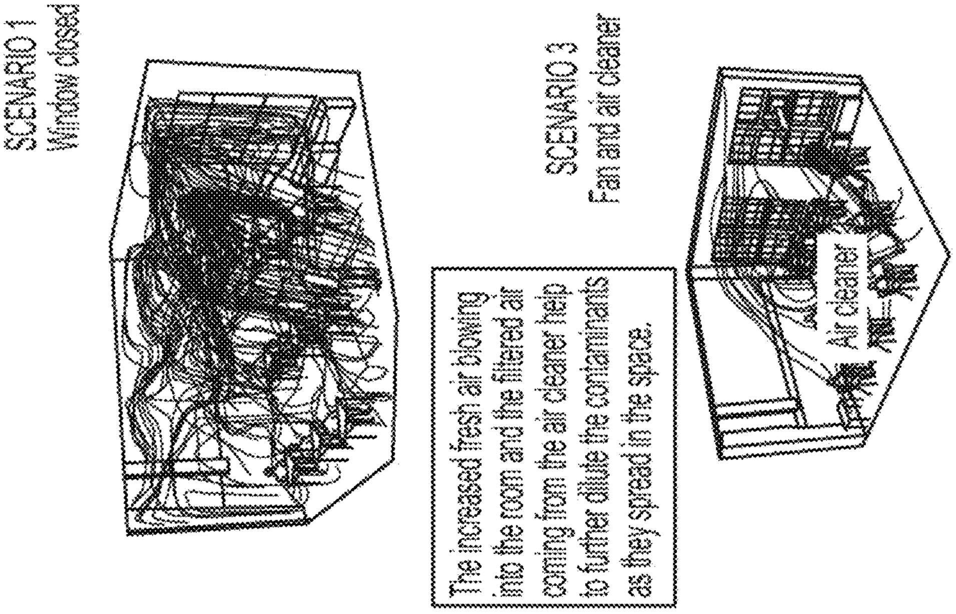
Figure 7B:
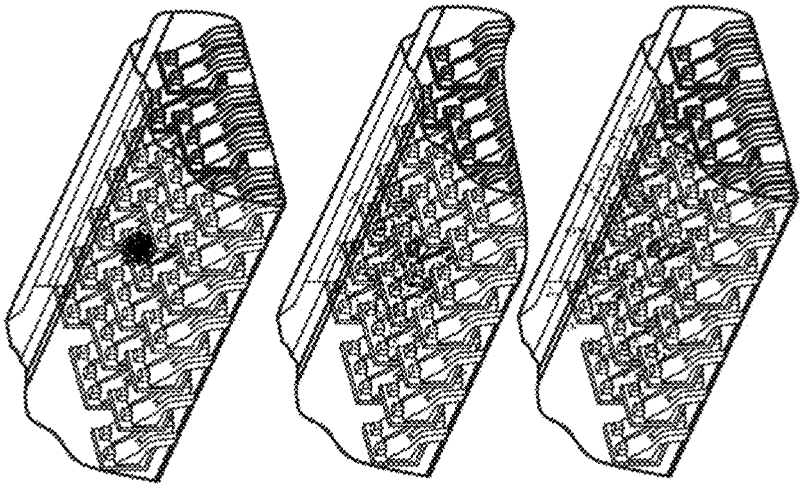
Figure 7C:
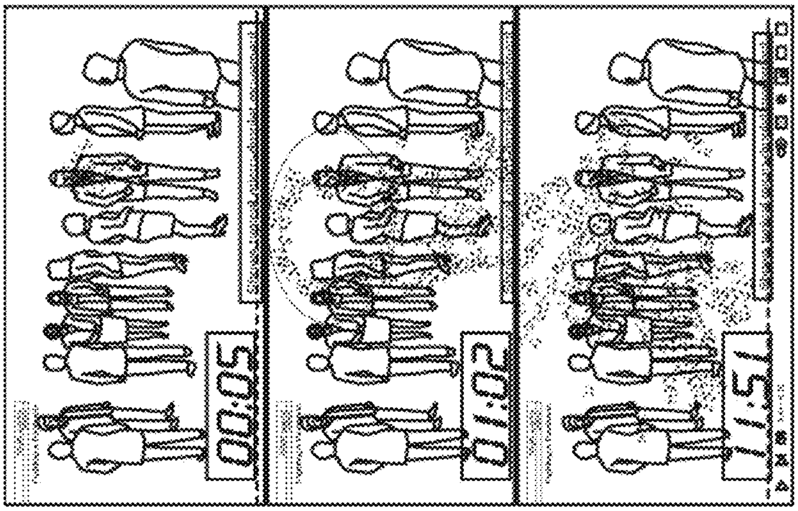

FIGS. 7A, 7B, and 7C depict example particle and ventilation flows within physical spaces in accordance with embodiments of the present disclosure.

Figure 8:
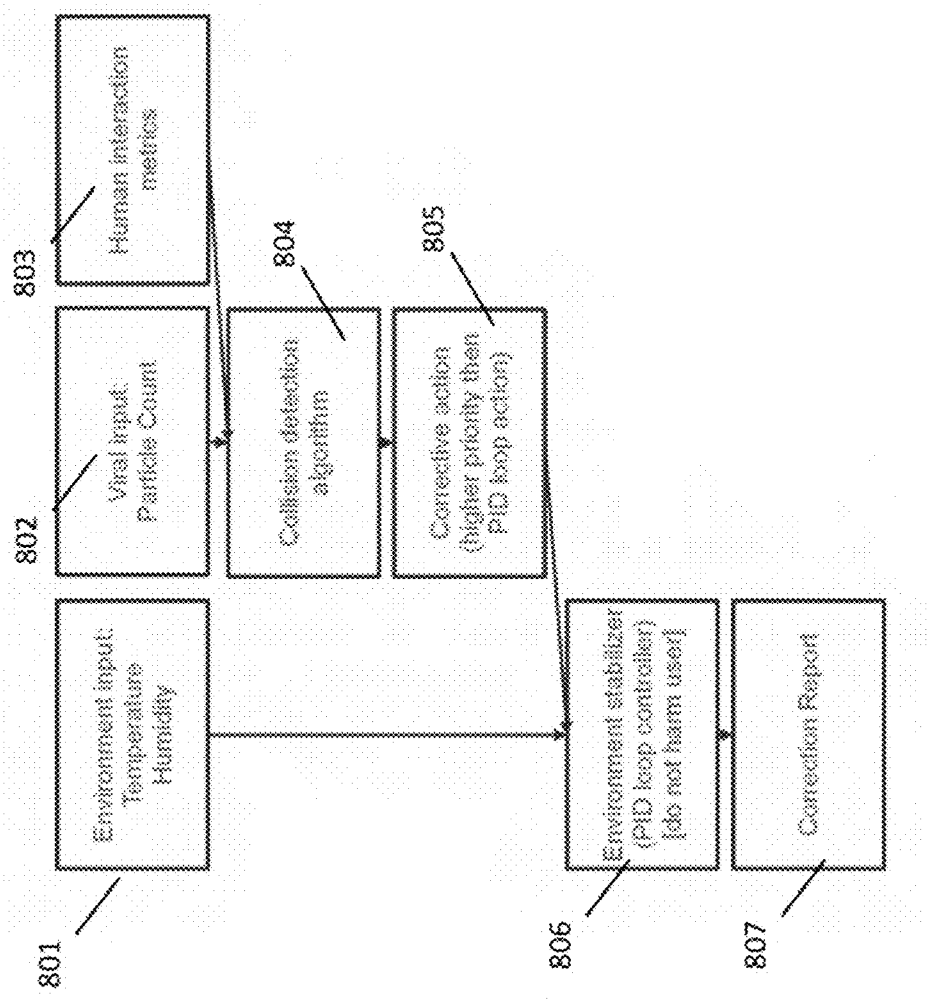

FIG. 8 depicts example operations for use in determining corrective actions in accordance with embodiments of the present disclosure.

Figure 9A:
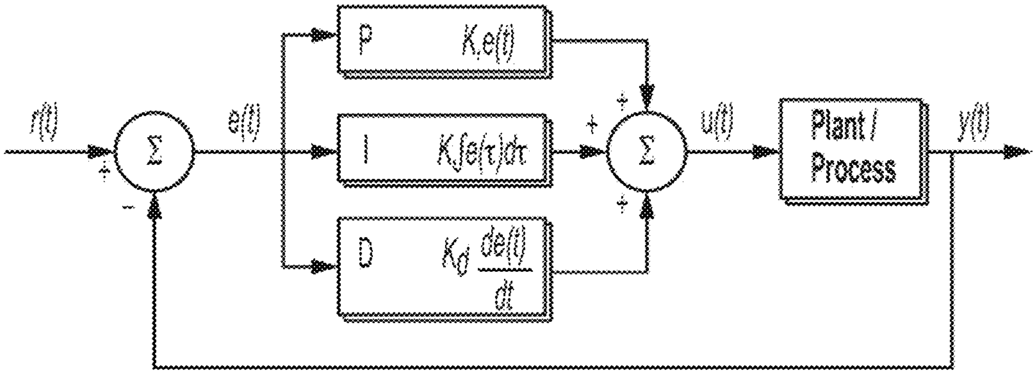
Figure 9B:
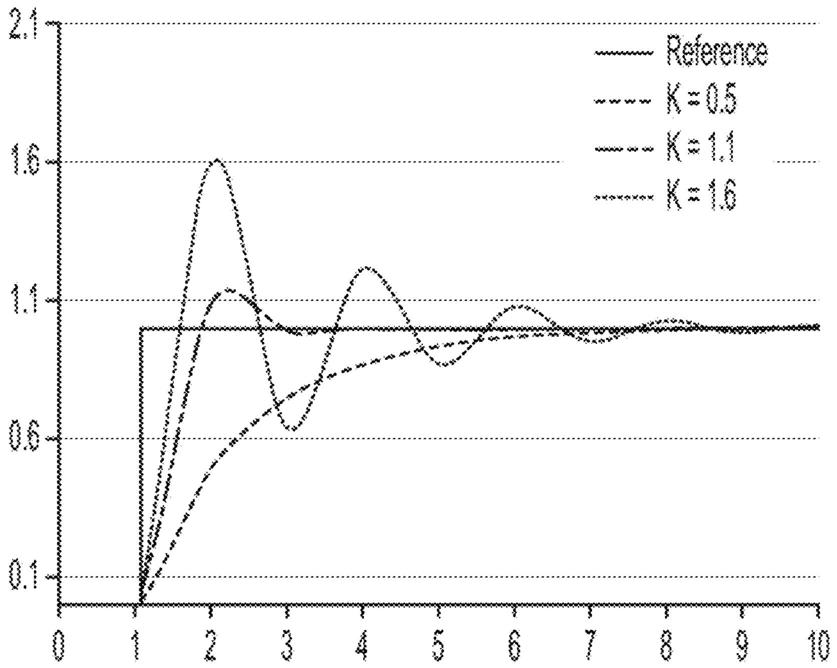

FIGS. 9A and 9B depict an example PID controller and response in accordance with embodiments of the present disclosure.

Figure 9C:
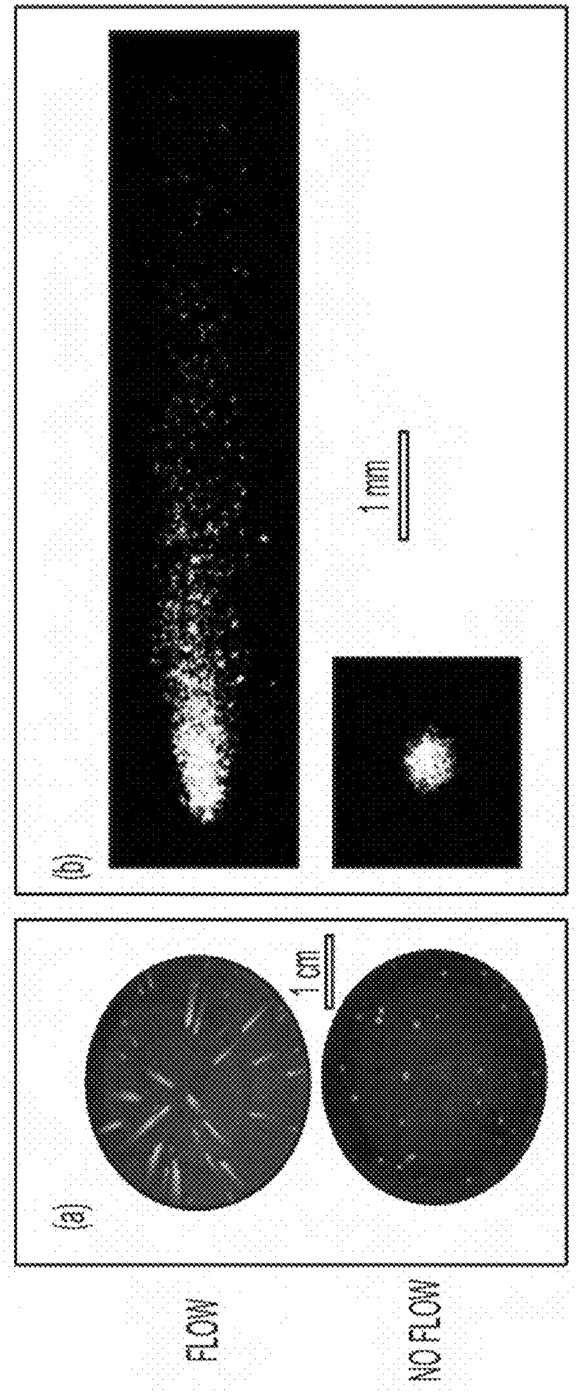

FIG. 9C depicts example particle flow in accordance with embodiments of the present disclosure.

Figure 10:
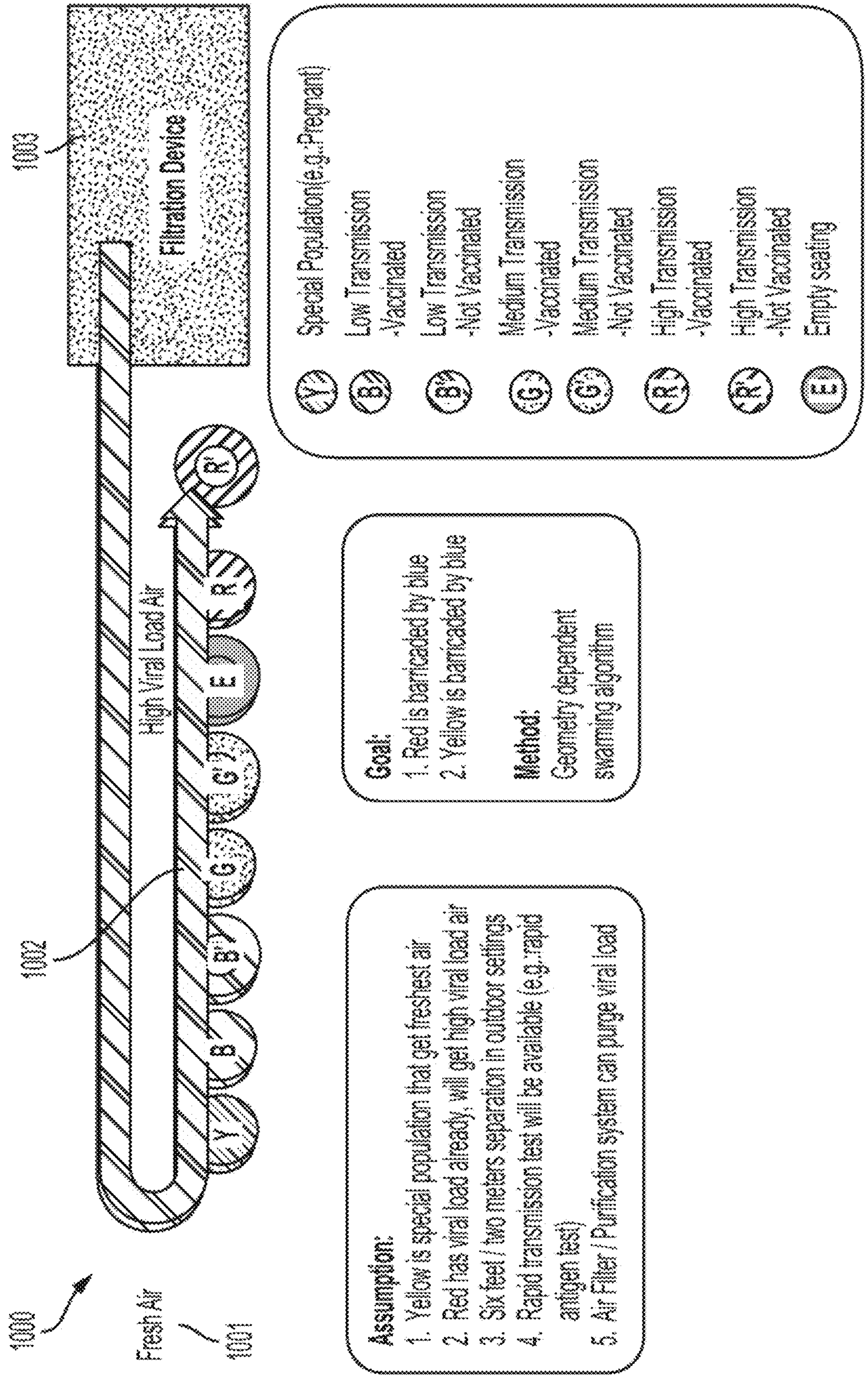

FIG. 10 depicts an example physical space allocation configuration in accordance with embodiments of the present disclosure.

Figure 11:
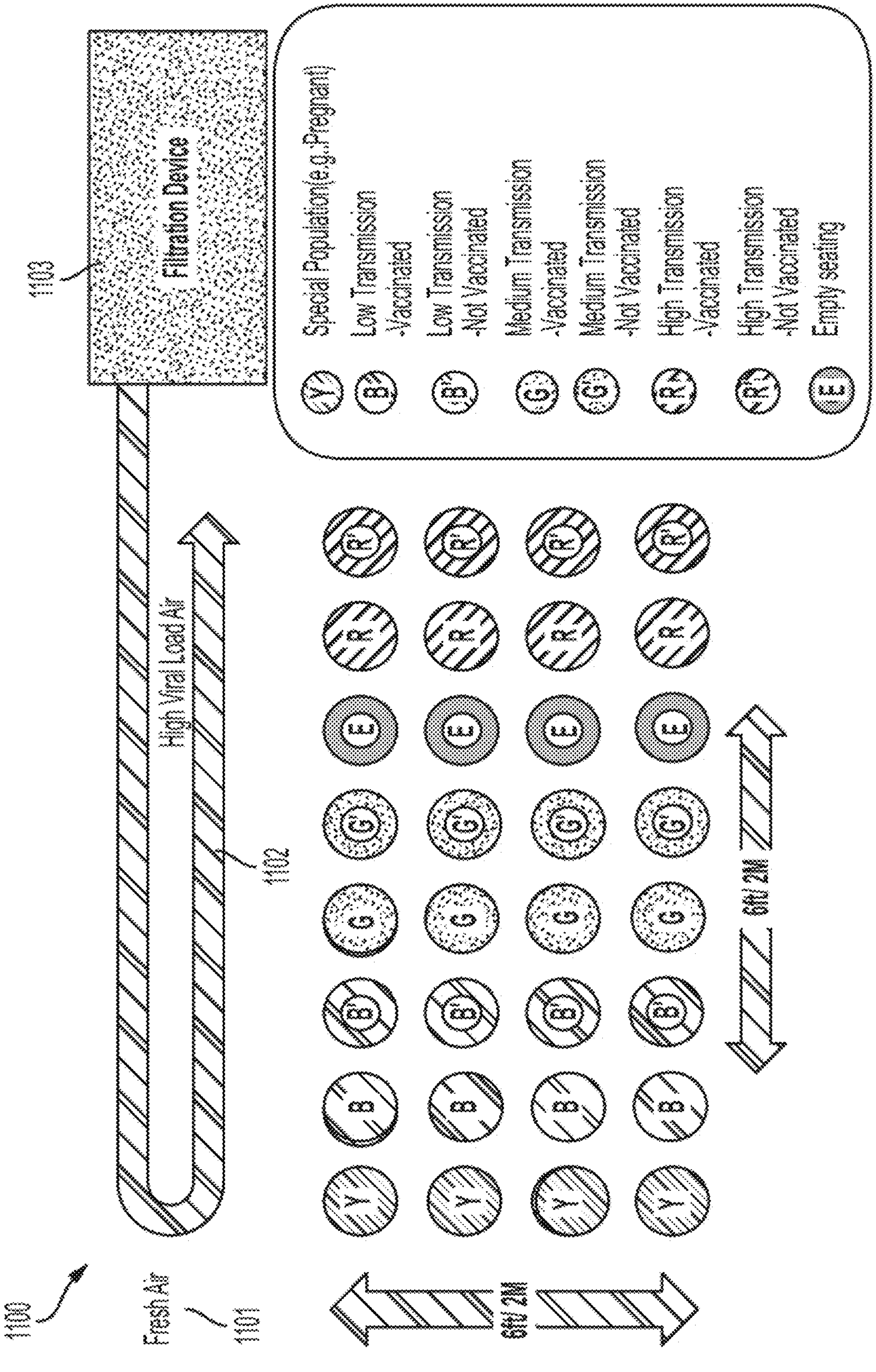

FIG. 11 depicts an example physical space allocation configuration in accordance with embodiments of the present disclosure.

Figure 12:
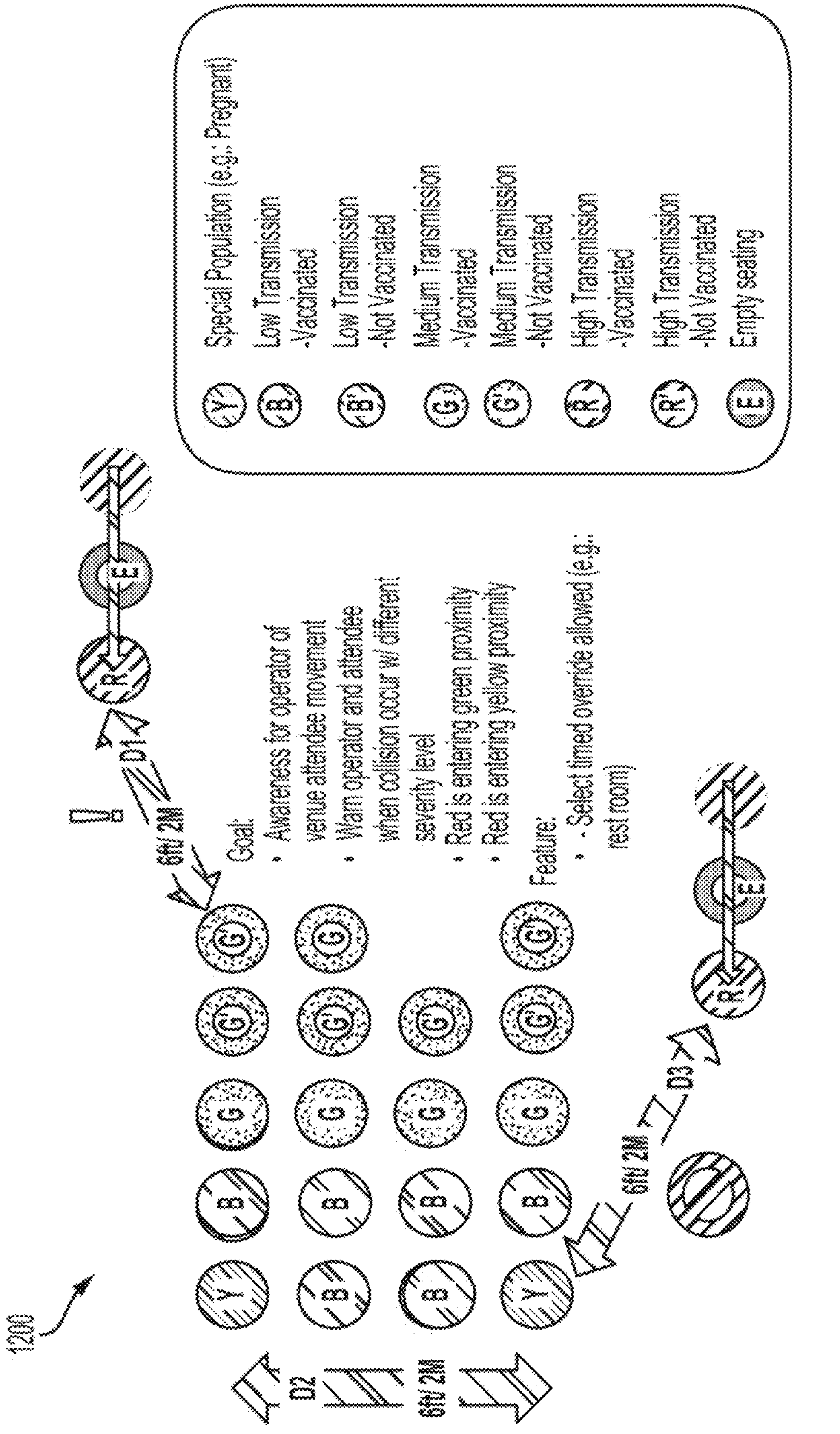

FIG. 12 depicts an example physical space allocation configuration in accordance with embodiments of the present disclosure.

FIG. 13 depicts an example physical space allocation schedule in accordance with embodiments of the present disclosure.

FIGS. 14A, 14B, 14C, and 14D illustrate example data flows for implementing various embodiments of the present disclosure.

Figure 15:
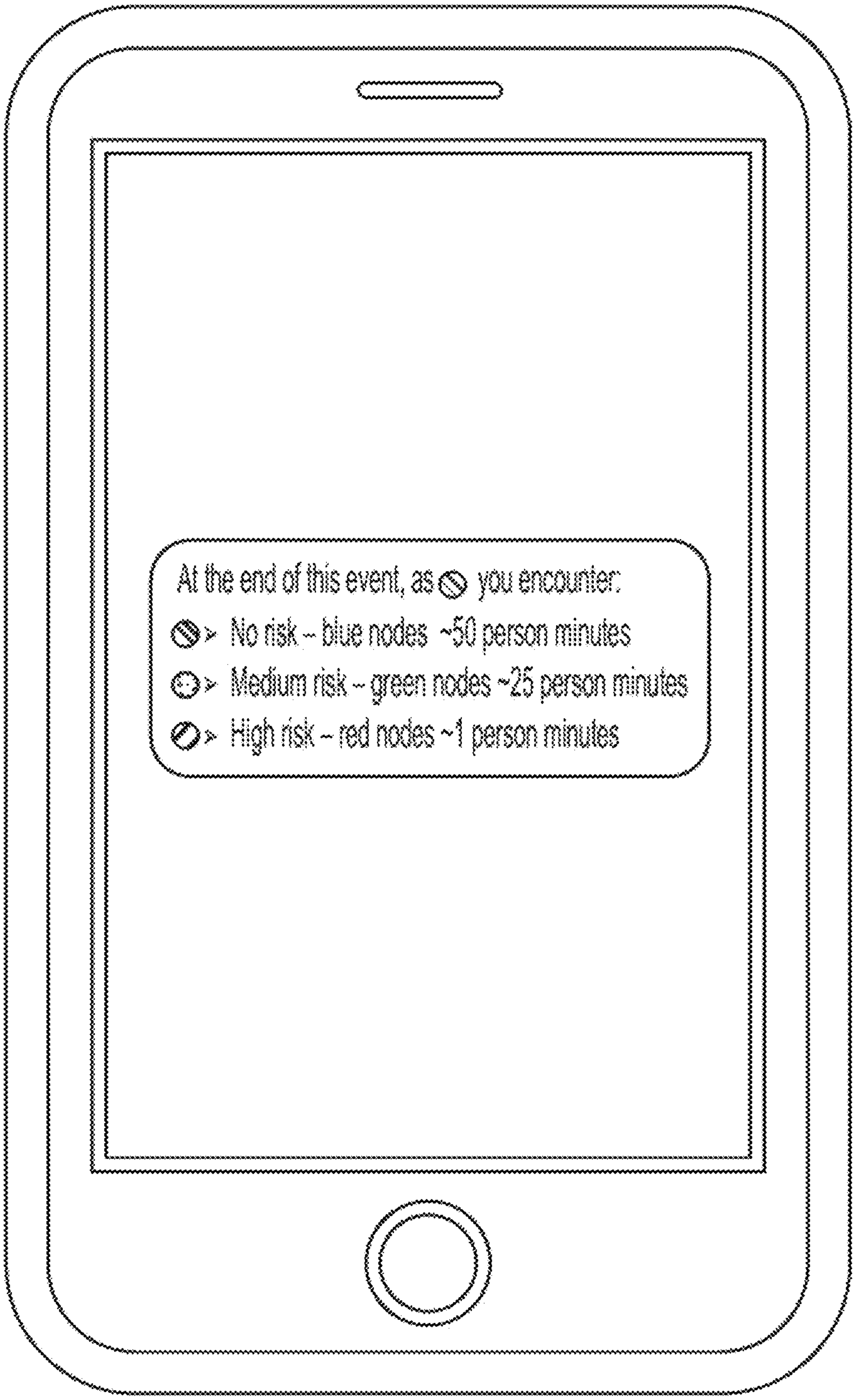

FIG. 15 illustrates an example collision report interface in accordance with some embodiments of the present disclosure.

DETAILED DESCRIPTION

Various embodiments of the present invention now will be described more fully hereinafter with reference to the accompanying drawings, in which some, but not all, embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense unless otherwise indicated. The terms "illustrative" and "exemplary" are used to be examples with no indication of quality level. Like numbers refer to like elements throughout.

I. OVERVIEW AND TECHNICAL IMPROVEMENTS

An immunization certification system identifying people who are immunized for various diseases or contagious viruses is not currently available. The current environment is demonstrating the need for people to prove they are not a threat to society based at least in part on normal everyday activities where contact in highly or lightly populated areas could cause others to become infected. While some businesses and medical facilities take precautionary measures where they perform a temperature check for those who may have a fever, this only reveals whether or not a person has one possible symptom of a disease. Some businesses also have designated times where people of a certain risk group are allowed to enter exclusively (e.g., dedicated hours for individuals 65 or older for grocery shopping).

In situations where people need to wear PPE (Personal Protective Equipment) gear to every visited establishment, embodiments herein enable the provision of proof of immunization to every establishment in an electronic certificate format that is easily scanned allowing entry to the establishment thereby minimizing the need for PPE gear. In situations where people are boarding a plane or booking airfare or a hotel room, embodiments herein enable provision of a certificate prior to boarding a plane or booking the hotel room as proof of immunization on check-in. In situations where a person is entering a facility whose patrons change frequently (e.g., gyms, fitness centers, schools), embodiments herein enable provision of, as part of a visit to the facility, an immunization certification. In situations where a person is entering a sporting/concert event (e.g., professional or local level), embodiments herein enable provision of an electronic certificate at the door or when buying ticket(s) to desired event. In situations where nursing care facilities are being opened for visitation and/or opening free range for residence, embodiments herein provide nursing care facilities the ability to download certificates proving immunization.

Embodiments herein are directed to the generation of a transfer risk (TR) score for each individual, where the transfer risk score represents a transmissibility measure associated with the individual that is based at least in part on immunization or immunity information or status of the individual (e.g., immunized based at least in part on vaccine, antibodies present, self-directed waiver as not immunized, physician directed waiver to not be immunized). Transfer risk (TR) scores may be associated with one or more specific viruses, diseases, conditions, or other transmissible infections. Transfer risk scores may be stored using public-private key pairs, one way hash, or other secure storage mechanisms.

In embodiments, an individual's transfer risk (TR) score may be compared to a threshold so that the individual may be assigned a color or grouping based at least in part on the TR score. For example, a color or grouping may be "yellow" and be associated with those individuals having a waiver for not having been immunized. Another color or grouping may be "blue" (representing a low TR score such as less than 10%). Another color or grouping may be "green" (representing a moderate TR score such as between 10% and 80%). Another color or grouping may be "red" (representing a high TR score such as greater than 80%). Thresholds may be adjusted according to regulatory changes (e.g., a state or county may require a high TR score % to operate, therefore the thresholds may be adjusted to reflect those regulations) or other factors. It will be appreciated that differing thresholds are within the scope of the present disclosure and the examples herein are for illustrative purposes.

TR score groupings may serve as the basis, along with other factors such as ventilation, venue specific parameters, or current transmissibility information, for designating or allocating physical space to individuals within a given venue or physical space. Designating or allocating physical space to individuals within the given venue or physical space may be accomplished according to optimization goals for seating allocations while minimizing infection risk or transmissibility between individuals associated with various levels of immunization certification or transfer risk (TR) scores. Non-limiting examples of venues or physical spaces may include airplanes, airports, restaurants or other eating establishments, performance venues (e.g., concert venues, theaters, and the like), transportation spaces or vehicles (e.g., taxis, Ubers, transit trains, and the like), or other public or private venues.

In embodiments, an individual associated with a client computing entity, upon arriving and situating within an assigned area, may receive alerts via the client computing entity (e.g., a mobile device equipped with the TR score or grouping information) to guide the individual into or away from particular areas based upon ventilation or transmissibility risk (e.g., based at least in part on the risk of "colliding" with or coming into too close of contact with a person or persons of a different TR score grouping).

In embodiments, corrective action may be automated according to detection of a number of individuals having particular TR scores or score groupings within a section of a venue or physical space in order to reduce the transmissibility risk posed by the individuals. For example, ventilation may be adjusted (e.g., improved or increased) in the section of the venue or physical space or ventilation may be adjusted in another section of the venue in order to increase overall ventilation of the venue or physical space. Ventilation may be improved by way of adjustments to an HVAC or other physical ventilation system associated with the venue or physical space. Ventilation may alternatively or additionally be improved by way of opening windows, doors, or other vents to increase air circulation within the venue or physical space.

Embodiments herein enable dynamic adjustment of physical space assignments and corrective actions based upon ever-changing transmissibility information and government regulations associated with known infectious diseases. For example, a given user may be associated with a first transfer risk score based upon a first set of transmissibility information and government regulations, yet when transmissibility information and/or government regulations are updated, the given user may be associated with a second transfer risk score that is different from the first transfer risk score. Embodiments herein overcome drawbacks associated with static physical space assignment systems by updating transfer risk scores based at least in part on real-time updates to transfer risk score vectors associated with users, by updating transfer risk score groupings based at least in part on real-time updates to transmissibility information and/or government regulations, and by dynamically initiating, in real-time, corrective actions designed to reduce transmission risk within a physical space based at least in part on changes in occupancy, transfer risk score groupings, locations of users within the physical space, ventilation of the physical space, viral loads, temperatures, particle counters, and more.

Embodiments herein further enable dynamic changes in view of businesses or legislatures making variable policies based at least in part on the analysis of the immunization certifications. For example, nursing home visitation policies may allow a larger number of visitors to be seen at the same time because an immunization certification has been presented. Embodiments herein further enable removal of limitations if a resident has been immunized (e.g., visitors could then be limited based at least in part on the visitor's immunization status. In various embodiments, government entities on the local, state or federal levels may be directly involved in the implementation.

II. DEFINITIONS

As used herein, the terms "data," "content," "digital content," "digital content object," "information," and similar terms may be used interchangeably to refer to data capable of being transmitted, received, and/or stored in accordance with embodiments of the present disclosure. Thus, use of any such terms should not be taken to limit the spirit and scope of embodiments of the present disclosure. Further, where a computing device is described herein to receive data from another computing device, it will be appreciated that the data may be received directly from another computing device or may be received indirectly via one or more intermediary computing devices/entities, such as, for example, one or more servers, relays, routers, network access points, base stations, hosts, and/or the like, sometimes referred to herein as a "network." Similarly, where a computing device is described herein to transmit data to another computing device, it will be appreciated that the data may be sent directly to another computing device or may be sent indirectly via one or more intermediary computing devices/entities, such as, for example, one or more servers, relays, routers, network access points, base stations, hosts, and/or the like.

The term "viral transfer risk management" refers to a plurality of specialized computing devices configured to reduce infectious exposure (e.g., viral transmission risk) within a physical space through a programmatic scheduling (e.g., allocation, notification, and corrective action) system that provides risk level assignments (e.g., physical space assignments) for a given time period of various immunized certification groups (e.g., transfer risk score groupings).

The term "user identifier" refers to one or more items of data by which a user may be uniquely identified. For example, a user identifier may comprise ASCII text, a pointer, a memory address, and the like.

The term "interaction" refers to an identifiable, non-transitory occurrence that has technical significance for system hardware and/or software. An interaction may be user-generated, such as keystrokes or mouse movements, or system-generated, such as program loading and errors.

The term "transfer risk score" refers to a programmatically generated score associated with a user identifier that represents a likelihood that a user associated with the user identifier will transmit viral or bacterial particles to one or more other users when the user is in a vicinity of the one or more other users. A transfer risk score may be based upon information stored in a transfer risk vector associated with the user identifier, as well as virus, bacteria, or disease specific information and/or regulations. A transfer risk vector may store one or more items of information associated with health or other data associated with the user identifier, such as immunity date, vaccination date, vaccination records, personal protective equipment (PPE) wearing habits, natural immunity, immunization declaration, one or more medical conditions, or medical history. Virus, bacteria or disease specific information and/or regulations may be associated with a current immunity timeframe, a vaccination incubation timeframe, a vaccination efficacy value, a vaccine expiration date, and the like.

The term "transfer risk vector" refers to a data structure comprising a plurality of transfer risk records, where the transfer risk vector is configured to store a plurality of attributes (e.g., transfer risk record values) in the transfer risk records. A transfer risk vector is associated with a user identifier.

The term "transfer risk record" refers to a data structure within a transfer risk vector configured for storing an attribute (e.g., as a transfer risk record value) associated with a user identifier. Examples of transfer risk record values that may be stored in transfer risk records include immunity date, vaccination date, vaccination records, personal protective equipment (PPE) wearing habits, natural immunity, immunization declaration, one or more medical conditions, or medical history.

The term "transfer risk score grouping" refers to one of a possible plurality of groupings of transfer risk scores according to dynamically defined risk thresholds. For example, a first transfer risk score grouping may be associated with transfer risk scores that are lower in relation to transfer risk scores associated with a second transfer risk score grouping. The dynamically defined risk thresholds may be configurable for a given physical space identifier and/or adjusted according to changes in transmissibility risk information and/or government regulations. In examples, transfer risk score groupings may be one of low, moderate, high, or waiver exception. In examples, a low transfer risk grouping may be associated with a transfer risk score of less than 10%, a moderate transfer risk grouping may be associated with a transfer risk score of at least 10% and less than 80%, a high transfer risk grouping may be associated with a transfer score of at least 80%, and a waiver exception transfer risk grouping may be associated with a transfer risk record having a transfer risk record value representing a waiver exception to having been immunized. A waiver exception may be based at least in part on a medical condition and/or a self-declared election to opt out of immunization. Embodiments herein may refer to the various transfer risk score groupings according to colors (e.g., blue, red, green, yellow) or other relative terms (e.g., low, moderate, high, waiver exception) for the purposes of illustration and not for the purposes of limiting transfer risk score groupings to the definitions presented herein.

The term "physical space" refers to a physical location at which live subjects may congregate for various reasons. Non-limiting examples of physical spaces include a restaurant, a venue, an arena, a stadium, a transport vehicle (e.g., plane, train, bus), a health care facility (e.g., nursing home, hospital, etc.) and the like. A physical space may have a plurality of physical space assignments within it that may be allocated for occupancy by a physical being (e.g., a user associated with a user identifier and/or a client computing entity).

The term "physical space assignment" refers to a subsection of a physical space that can be occupied by a physical being or that can be left unoccupied by physical beings. Examples of physical units include seats, tables, and sections. A physical space assignment may be associated with one or more dimensions. The one or more dimensions may comprise one or more of a depth, a width, a height, or a space radius. A space radius may be a cushion of free space surrounding a physical space assignment. A physical space assignment may be available for allocation to a user identifier, or reserved (e.g., unavailable for allocation to a user identifier for various reasons).

The term "physical space identifier" refers to one or more items of data by which a physical space may be uniquely identified. For example, a physical space identifier may comprise ASCII text, a pointer, a memory address, and the like.

The term "physical space parameters" refers to attributes associated with a physical space associated with a physical space identifier, where the physical space parameters may have an impact on viral risk transmission. Examples of physical space parameters include physical space shape (e.g., round, rectangular, arc, square, and the like), physical space square footage (e.g., also possibly based upon dimensions of the physical space such as length, width, height, and the like), physical space restricted areas (e.g., areas within a physical space unauthorized users are not allowed to occupy), physical space openings (e.g., doors, windows, vents, and the like), physical space ventilation pattern (e.g., how air travels within the physical space, including a direction from a physical space ventilation pattern starting point such as a fan, a vent, or other ventilation source and to a physical space ventilation pattern end point), physical space ventilation capabilities (e.g., a number and type of fans, HVAC capabilities, airflow based at least in part on multiple windows or doors, and the like), available physical space assignments (e.g., physical space assignments that have not been allocated to user identifiers), or reserved physical space assignments (e.g., physical space assignments that have been allocated to user identifiers).

The term "proximity" refers to a distance between a first client computing entity and a second client computing entity that is considered relevant to viral transmissibility risk. For example, depending upon information known about the transmissibility of a given virus or infectious disease, a proximity within which the risk of transmission is relevant may be six feet. In other examples, a proximity may be greater than six feet, and may be based at least in part on physical space parameters and transmissibility risk information (e.g., if a physical space has little to no ventilation, transmissibility risk may be greater and thus a proximity may be reduced).

The term "collision potential notification" refers to a message (e.g., a push notification, a mobile notification, an electronic message, an SMS, a text message, an electronic mail message) for transmission to a client computing entity and configured for display via the client computing entity, where the collision potential notification comprises instructions for rendering a graphical representation of a warning that a user associated with the client computing entity may come in contact with one or more other users associated with one or more other client computing entities such that the user would be exposed to an increase viral transmission risk by coming into contact with or into close proximity with the one or more other users. A collision potential notification may be generated and transmitted based upon detected locations associated with the client computing entity and the one or more other client computing entities, as well as a detected velocity (e.g., a direction and speed of travel) associated with the client computing entity and the one or more other client computing entities.

The term "distributed ledger" refers to a consensus of replicated, shared, and synchronized digital data spread across several nodes (devices) on a peer-to-peer network, where each replicates and saves an identical copy of the ledger and updates itself independently. When a ledger update happens, each node constructs the new transaction, and then the nodes vote by consensus algorithm on which copy is correct. Once a consensus has been determined, all the other nodes update themselves with the new, correct copy of the ledger. Security is accomplished through cryptographic keys and signatures.

The term "distributed ledger record" refers to a record or transaction of a distributed ledger.

The term "public-private key pair" refers to a pair of keys for use in cryptography. Public keys may be known to others; private keys may never be known by any except the owner. The generation of such key pairs depends on cryptographic algorithms which are based at least in part on mathematical problems termed one-way functions. Effective security requires keeping the private key private; the public key can be openly distributed without compromising security.

The term "transfer risk transcript interface" refers to a collection of graphical interface elements for rendering representations of a transfer risk score, a transfer risk score grouping, or one or more transfer risk record values associated with a user identifier.

The term "safe physical distance threshold" refers to a physical distance (among other possible measures) that is preferred to be maintained between human beings or groups of human beings. Examples of safe physical distance thresholds may include social distancing measures such as six feet during the COVID-19 pandemic. The safe physical distance threshold may comprise a distance, and the distance specified may differ from time to time and from country to country. Various embodiments may implement safe physical distance thresholds by automatically positioning empty physical space assignments or other known empty areas adjacent to and/or surrounding physical space assignments allocated for use. Accordingly, various embodiments may store data indicative of the dimensions of each physical space assignment (e.g., a width, depth, height of a seat or table), such that the dimensions of each physical space assignment may be correlated with distances specified within safe physical distance threshold. Similarly, dimensions of known non-occupied areas (e.g., aisles, restricted areas, restrooms, and/or the like) within a physical space may be considered when determining an optimal allocation of physical space assignments and/or corrective movement recommendations, corrective actions, and the like.

The term "corrective movement recommendation" refers to instructions to a user representing a recommendation that the user, being associated with a client computing entity and a particular location or velocity, move to a different location or avoid coming into contact with one or more other users associated with one or more other client computing entities. The user may wish to avoid coming into contact with (e.g., colliding with, or coming into close or other proximity with) the one or more other users because the one or more other users may be associated with transfer risk score groupings that may be adverse to the user (e.g., the user may be at increased risk of viral or other infectious transmission from the one or more other users based at least in part on higher transfer risk score groupings or transfer risk scores associated with the one or more other users).

The term "risk ceiling" refers to a programmatically generated value representing a maximum amount of transmission risk to be tolerated by or allocated within a physical space. The risk ceiling represents a configurable safety threshold that can be adjusted according to physical space parameters and/or transmission risk information. For example, an operator of a physical space may adjust a risk ceiling based at least in part on likelihoods of collisions (e.g., the likelihood that users associated with varying transfer risk score groupings will come into contact with each other; e.g., this may be based upon physical space parameters). By way of further example, an operator of a physical space may adjust a risk ceiling so that only a certain number of user identifiers associated with a given transfer risk score grouping (e.g., high risk) are able to have physical space assignments allocated to them. By way of further example, a risk ceiling may enable dynamic allocation of physical space assignments according to an understanding of how many physical space assignments have already been allocated to user identifiers associated with differing transfer risk score grouping (e.g., a given area or room of a physical space may only have capacity for one more high transfer risk score grouping user identifier, while another area or room of a physical space may need to leave a physical space assignment available in order to allocate it to the next user identifier associated with a moderate transfer risk score grouping so that the risk ceiling is not exceeded).

The term "physical space assignment interface" refers to a collection of graphical interface elements for rendering representations of a physical space assignment associated with a user identifier.

The term "corrective action" refers to automated actions that can be initiated in order to minimize transmission risk within a physical space. Non-limiting examples of corrective actions include adjusting air filtration associated with the physical space, adjusting sanitation associated with the physical space, adjusting exhaust associated with the physical space, or transmitting a collision potential notification to one or more client computing entities of the plurality of client computing entities. Adjusting air filtration associated with the physical space may include controlling a HEPA filter fan. Adjusting sanitation associated with the physical space may include one or more of activating one or more UV light stations within the physical space or activating one or more anti-bacterial spray stations within the physical space. Adjusting exhaust associated with the physical space may include one or more of exhaust redirection, HVAC zone control adjustments, or automatic window adjustments.

The term "sensor" refers to a device, module, machine, or subsystem whose purpose is to detect events or changes in its environment and send the information to other computing entities. Examples of sensors include a particle counter (e.g., used for monitoring and diagnosing particle contamination within the air or environment), a camera, a microphone, a thermal camera, a client computing entity configured to detect viral transmission risk statements based at least in part on speech detection and natural language processing, or regression based sensors configured to detect changes in skin color.

The term "viral load" refers to a numerical expression of the quantity of virus in a given environment or person.

The term "particle count threshold" refers to a maximum amount of particle contamination that is tolerable for a given physical space.

The term "body temperature threshold" refers to a maximum body temperature associated with users within a physical space that is tolerable for the given physical space.

The term "collision report interface" refers to a collection of graphical interface elements for rendering representations of a collision report information associated with a user identifier. A collision report interface may include graphical representations of one or more of accumulated viral input and collision calculations, corrective actions that were initiated during a time window within which the first client computing entity was within the physical space, or proposed medical actions to be performed in accordance with a first user identifier associated with the first client computing entity.

III. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report-writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media includes all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations. Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM ARCHITECTURE

FIG. 1 is a schematic diagram of an example architecture 100 for performing viral transfer risk management. The architecture 100 includes a viral transfer risk management system 101 configured to receive viral transfer risk management requests from client computing entities 102, process the viral transfer risk management requests to generate viral transfer risk management recommendations and provide the generated recommendations to the client computing entities 102, and automatically perform viral transfer risk management-based actions based at least in part on the generated recommendations.

In some embodiments, viral transfer risk management system 101 may communicate with at least one of the client computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The viral transfer risk management system 101 may include a viral transfer risk management computing entity 106 and a storage subsystem 108. The viral transfer risk management computing entity 106 may be configured to receive viral transfer risk management requests from one or more client computing entities 102 and process the viral transfer risk management requests to generate viral transfer risk management recommendations corresponding to the viral transfer risk management requests, provide the generated recommendations to the client computing entities 102, and automatically perform viral transfer risk management-based actions based at least in part on the generated recommendations.

The storage subsystem 108 may be configured to store input data used by the viral transfer risk management computing entity 106 to perform viral transfer risk management. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Viral Transfer Risk Management Computing Entity

FIG. 2 provides a schematic of a viral transfer risk management computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the viral transfer risk management computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the viral transfer risk management computing entity 106 may include, or be in communication with, one or more processing elements 205 (also referred to as processors, processing circuitry, and/or similar terms used herein interchangeably) that communicate with other elements within the viral transfer risk management computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the viral transfer risk management computing entity 106 may further include, or be in communication with, non-volatile media (also referred to as non-volatile storage, memory, memory storage, memory circuitry and/or similar terms used herein interchangeably). In one embodiment, the non-volatile storage or memory may include one or more non-volatile storage or memory media 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the resource allocation optimization computing entity 106 may further include, or be in communication with, volatile media (also referred to as volatile storage, memory, memory storage, memory circuitry and/or similar terms used herein interchangeably). In one embodiment, the volatile storage or memory may also include one or more volatile storage or memory media 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the viral transfer risk management computing entity 106 with the assistance of the processing element 205 and operating system.

As indicated, in one embodiment, the viral transfer risk management computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the resource allocation optimization computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the viral transfer risk management computing entity 106 may include, or be in communication with, one or more input elements, such as a keyboard input, a mouse input, a touch screen/display input, motion input, movement input, audio input, pointing device input, joystick input, keypad input, and/or the like. The viral transfer risk management computing entity 106 may also include, or be in communication with, one or more output elements (not shown), such as audio output, video output, screen/display output, motion output, movement output, and/or the like.

Exemplary Client Computing Entity

FIG. 3 provides an illustrative schematic representative of a client computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 can be operated by various parties. As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the viral transfer risk management computing entity 106. In a particular embodiment, the client computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the resource allocation optimization computing entity 106 via a network interface 320.

Via these communication standards and protocols, the client computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to one embodiment, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the client computing entity's 102 position in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the viral transfer risk management computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the client computing entity 102. As indicated, this may include a user application that is resident on the entity or accessible through a browser or other user interface for communicating with the viral transfer risk management computing entity 106 and/or various other computing entities.

In another embodiment, the client computing entity 102 may include one or more components or functionality that are the same or similar to those of the viral transfer risk management computing entity 106, as described in greater detail above. As will be recognized, these architectures and descriptions are provided for exemplary purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. EXEMPLARY SYSTEM OPERATIONS

As described below, various embodiments of the present invention provide methods, apparatus, systems, computing devices, computing entities, and/or the like for viral transfer risk management.

Embodiments herein enable the provision of certification by a user by way of a client computing entity (e.g., mobile device) or the provision of access to the user's certified records so that the user may be allowed entry to a desired venue or physical space. The issuing authority may provide the certificate based at least in part on credentials associated with the requesting entity as well as the user to whom immunizations are or were given. The user can allow other entities access for a time frame to download the certificate as proof required to engage in activities with the desired entity.

Embodiments herein allow entities to request an electronic certification based at least in part on transmissibility to verify a given person has been immunized for a specific disease or virus or specified list of diseases or viruses. The electronic certification can be used to calculate transmissibility criteria based at least in part on regulatory and scientific advancement (e.g., a transfer risk (TR) score). The TR score or transfer risk score grouping (e.g., a color, level, or label) assigned to a transfer risk score grouping) can function as proof for entry to numerous business events or other events where close proximity to others may not be prevented. The certificate and "color" may be downloaded to a person's mobile device and automatically scanned for proof of adherence to health code regulations.

In embodiments, a transfer risk (TR) score may serve as an assessment of various transmissibility risk criteria associated with a given user (e.g., or patient). For example, the TR score may include assessment of patient (e.g., user) received/provided TR information (e.g., whether through vaccination, PPE wearing habit, develop natural immunity, self-declaration as not immunized or weak immunity, and the like). The patient information is stored (e.g., as a transfer risk vector associated with a user identifier associated with the patient or user) in a data repository. In embodiments, the transfer risk vector may be stored using decentralized storage or a distributed ledger (e.g., blockchain). In embodiments, a public-private key pair is generated for each transfer risk vector (e.g., or each transfer risk score calculation) for authentication. In embodiments, each transaction may be stored as a one-way hash (e.g., immutable in the blockchain). Immutability enables historical records.

In embodiments, the public-private key pair enable access through a client computing entity (e.g., via a mobile app, accessible by restaurant/airline/possible emergency medical practitioner, and the like). In embodiments, since a user owns the private key, the user is able to demonstrate ownership of records. In embodiments, a user may use the private key to decrypt their record from the blockchain (e.g., or distributed ledger) records. Upon decryption of the record, one or more transfer risk score records (e.g., generation of TR score, transfer risk score grouping information, transfer risk vector records, and the like) may be displayed via the client computing device (e.g., in the form of a transcript, JSON, XML, and the like).

In embodiments, an apparatus may be configured to retrieve a first user identifier associated with a first client computing entity, determine, based at least in part on a first transfer risk score associated with the first user identifier, a first transfer risk score grouping for the first user identifier, and, based at least in part on the first transfer risk score grouping, and physical space parameters associated with a physical space identifier, allocate a first physical space assignment within a physical space associated with the physical space identifier to the first user identifier associated with the first client computing entity.

FIG. 4 depicts an example physical space allocation configuration in accordance with embodiments of the present disclosure. In FIG. 4, a physical space 400 (e.g., a restaurant) may be divided into several distinct areas 401, 402, 403, 404, 405, 406, and 407. Within each of the areas, several physical space assignments (e.g., tables, seats at the tables) may be available for allocation to users associated with user identifiers and client computing entities. It will be appreciated that each user may be associated with a transfer risk score grouping of low transmission risk (e.g., indicated by 408 in FIG. 4), medium or moderate transmission risk (e.g., indicated by 409 in FIG. 4), special population or waiver exception (e.g., indicated by 410 in FIG. 4), or high transmission risk (e.g., indicated by 411 in FIG. 4). It can be seen in FIG. 4 that an area, such as area 405, may have its physical space assignments primarily allocated to users associated with transfer risk score groupings within the medium 409 grouping. Similarly, area 401 may have physical space assignments primarily allocated to users associated with transfer risk score groupings within the medium 409 and low 408 groupings. Similarly, area 403 may have physical space assignments primarily allocated to users associated with transfer risk score groupings within the special 410 and low 408 groupings. Similarly, area 402 may have physical space assignments primarily allocated to users associated with transfer risk score groupings within the special 410 and low 408 groupings. Similarly, area 406 may have physical space assignments primarily allocated to users associated with transfer risk score groupings within the low 408 grouping. Similarly, area 404 may have physical space assignments primarily allocated to users associated with transfer risk score groupings within the high 411 grouping. Similarly, area 405 may have physical space assignments primarily allocated to users associated with transfer risk score groupings within the medium 409 grouping. It will be appreciated that different tables within an area may have seats at them that may be allocated to users associated with transfer risk score groupings within different groupings. Area 407 may be considered unavailable for allocation as it may be associated with restrooms.

FIG. 5 depicts an example physical space allocation schedule in accordance with embodiments of the present disclosure. In FIG. 5, a physical space allocation schedule 500 may be associated with a physical space (e.g., a restaurant) and a physical space identifier. The physical space allocation schedule 500 may be organized according to time segments 501, where each time segment is associated with a risk ceiling 503 (as defined herein) and a current risk score 502. The current risk score 502 for any given time segment 501 may be adjusted when a physical space assignment is allocated to a user based at least in part on the transfer risk score grouping associated with the user. The physical space allocation schedule 500 enables visualization and evaluation of whether any given time segment 501 is at risk of exceeding its associated risk ceiling 503 based at least in part on its current risk score 502.

FIG. 6 depicts an example physical space allocation configuration in accordance with embodiments of the present disclosure. In FIG. 6, a physical space 600 (e.g., an airplane) may be divided into several distinct areas 602A, 602B. Within each of the areas, several physical space assignments (e.g., seats) may be available for allocation to users associated with user identifiers and client computing entities. It will be appreciated that each user may be associated with a transfer risk score grouping of low transmission risk (e.g., indicated by 608 in FIG. 6), medium or moderate transmission risk (e.g., indicated by 609 in FIG. 6), special population or waiver exception (e.g., indicated by 610 in FIG. 6), or high transmission risk (e.g., indicated by 611 in FIG. 6).

FIGS. 7A, 7B, and 7C depict example particle and ventilation flows within physical spaces in accordance with embodiments of the present disclosure. In FIG. 7A, increased fresh air blowing into a physical space (e.g., a room) coming from an air cleaner is shown to help dilute contaminants as they spread in the physical space. In FIG. 7B, contaminants are shown as dispersing into a physical space (e.g., an airplane) after being emitted by a first person and then spread across multiple other people within the physical space. In FIG. 7C, micro-droplet movement is depicted over time.

FIG. 8 depicts example operations for use in determining corrective actions in accordance with embodiments of the present disclosure. In FIG. 8, corrective action 805 may be determined based at least in part on viral input (e.g., particle count) 802 associated with a physical space, human interaction metrics 803, and collision detection analyses 804 (e.g., movement among users associated with client computing entities and their respective transfer risk score groupings). Environmental stabilizers 806 (e.g., a PID loop controller) may be determined based upon the corrective actions 805 as well as environmental input 801 (e.g., temperature, humidity, and the like). A correction report 807 may be generated based upon corrective actions that were initiated and completed.

FIGS. 9A and 9B depict an example PID controller and response in accordance with embodiments of the present disclosure. In FIG. 9A, a block diagram of a PID controller is shown in a feedback loop, where r(t) is the desired process value or setpoint (SP), and y(t) is the measured process value (PV). FIG. 9B depicts a response of PV to step change of SP vs time. A PID controller may be used to determine corrective actions in various embodiments of the present disclosure. FIG. 9C depicts example particle flow in accordance with embodiments of the present disclosure. In FIG. 9C, formation of flow and no flow of an example virus is shown.

FIG. 10 depicts an example physical space allocation configuration in accordance with embodiments of the present disclosure. In FIG. 10, a physical space allocation configuration 1000 may be designed according to a direction of high viral load air 1002 from a filtration device 1003, toward fresh air 1001, past users associated with varying transfer risk score groupings (e.g., Y, B, B', G, G', E, R, and R') and back to the filtration device 1003.

FIG. 11 depicts an example physical space allocation configuration in accordance with embodiments of the present disclosure. In FIG. 11, a physical space allocation configuration 1100 may be designed according to a direction of high viral load air 1102 from a filtration device 1103, toward fresh air 1101, past users associated with varying transfer risk score groupings (e.g., Y, B, B', G, G', E, R, and R') and back to the filtration device 1103. The users may be situated in relation to one another according to their associated transfer risk score groupings within a space having varying dimensions (e.g., 6 ft.×6 ft.).

FIG. 12 depicts an example physical space allocation configuration in accordance with embodiments of the present disclosure. In FIG. 12, a physical space allocation configuration 1200 may be designed according to users associated with varying transfer risk score groupings (e.g., Y, B, B', G, G', E, R, and R'). For example, users associated with a high risk of transmission (e.g., R) may be kept a defined distance (e.g., D1, D3) away from the rest of the users within the defined space (e.g., having a width of 6 ft.).

FIG. 13 depicts an example physical space allocation schedule in accordance with embodiments of the present disclosure. In FIG. 13, a physical space allocation schedule 1300 may be associated with a physical space (e.g., a restaurant) and a physical space identifier. The physical space allocation schedule 1300 may be organized according to time segments 1301, where each time segment is associated with a risk ceiling 1304 (as defined herein) and a current risk score 1303. The current risk score 1303 for any given time segment 1301 may be adjusted when a physical space assignment is allocated to a user based at least in part on the transfer risk score grouping 1302 associated with the user. The physical space allocation schedule 1300 enables visualization and evaluation of whether any given time segment 1301 is at risk of exceeding its associated risk ceiling 1304 based at least in part on its current risk score 1303 and the transfer risk score groupings 1302 associated with physical space assignments allocated within the given time segment 1301.

FIGS. 14A, 14B, 14C, and 14D illustrate example data flows for implementing various embodiments of the present disclosure.

Figure 14A:
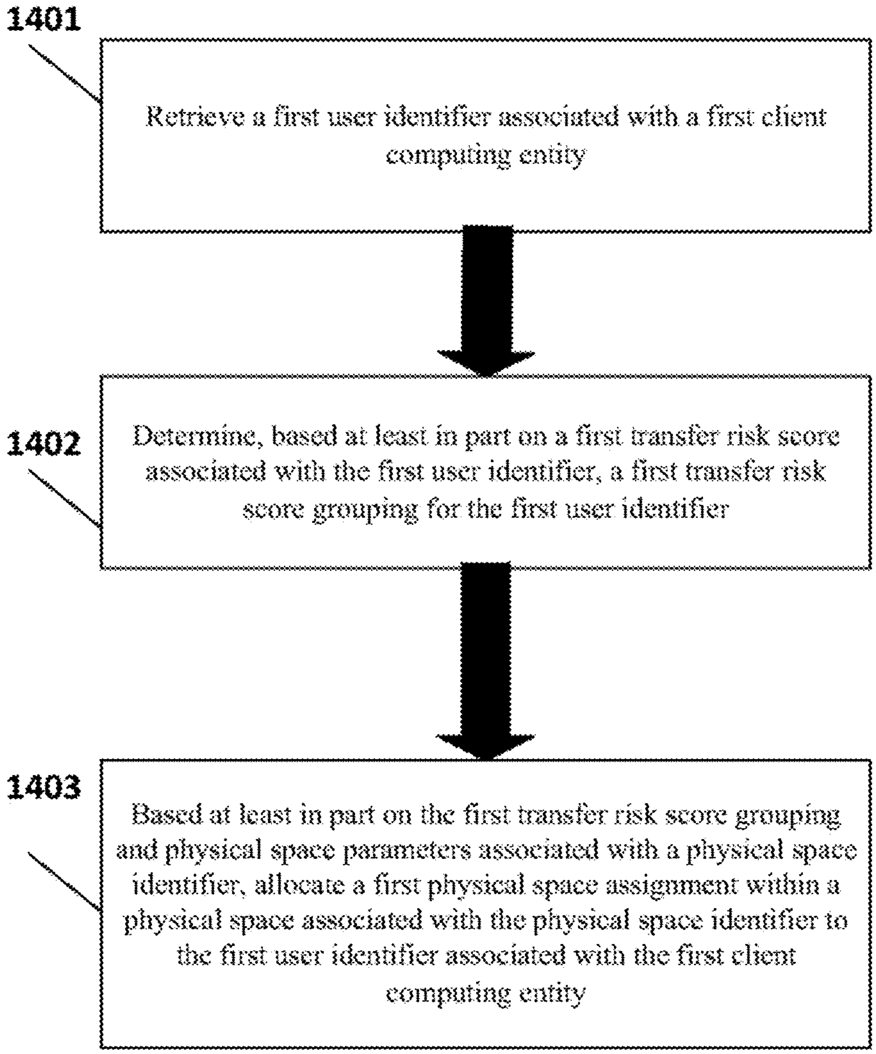

In FIG. 14A, an apparatus (e.g., such as viral transfer risk management computing entity 106) may be configured to retrieve 1401 a first user identifier associated with a first client computing entity (e.g., such as client computing entity 102). The apparatus may be further configured to determine 1402, based at least in part on a first transfer risk score associated with the first user identifier, a first transfer risk score grouping for the first user identifier. The apparatus may be further configured to, based at least in part on the first transfer risk score grouping and physical space parameters associated with a physical space identifier, allocate 1403 a first physical space assignment within a physical space associated with the physical space identifier to the first user identifier associated with the first client computing entity.

In various embodiments, allocating physical space assignments is performed in accordance with minimizing infection or transmissibility risk between various levels of certifications or transfer risk score groupings. Minimizing infection or transmissibility risk may minimize exposure for an entity and based at least in part on scheduling and risk level assignments (e.g., transfer risk score groupings). In embodiments, users with similar transfer risks (e.g., transfer risk scores or transfer risk score groupings) may be safely seated close (e.g., within a given proximity) to each other without having to comply with a safe distancing protocol (e.g., six feet of social distancing with respect to COVID-19).

In embodiments, allocating physical space assignments may involve defining a geometrical boundary associated with the physical space (e.g., a plane may be rectangular, a concert venue may be a semi-circular arc, and the like). Physical space assignments may be defined within the geometrical boundary. Either or both of a transfer risk score or a transfer risk score grouping is obtained for each user for which physical space assignment should be allotted or allocated. Allocation of physical space assignments may then be performed in accordance with a goal of minimizing exposure among user (e.g., for example, this may be performed according to a variation of a swarm algorithm; e.g. the lead bird that is in a V geometry reduces effort for those adjacent). Allocation of physical space assignments may also include initially randomly allocating physical space assignments as an initial “guess,” and then iteratively revising the allocation of physical space assignments to reduce exposure or transmissibility risk overall. Random allocation may be performed according to a geometrical feature to optimize this initial assignment (e.g., airplane seating may be linear). Allocation of physical space assignments, in various embodiments, may be performed according to assigning at a start and end of ventilation flow or pattern (e.g., the goal may be for airflow to flow from yellow (e.g., or waiver/exception)>blue (e.g., or low transmission risk) >green (e.g., or moderate transmission risk)>red (e.g., or high transmission risk). In embodiments, blue (e.g., or low transmission risk) may be used as a buffer between red (e.g., or high transmission risk) and other population (e.g., or waiver/exception) whenever possible. In embodiments, allocating physical space assignments may further be based at least in part on historical transmission rate or ventilation data. In embodiments, manual allocation of physical space assignments may be possible.

In embodiments, other optimizations for allocating physical space assignments may include grouping all of the known red (e.g., users associated with high transmission risk) at the end of a ventilation zone, scattering yellow (e.g., users associated with waiver/exception transmissibility risk) in the beginning of a ventilation zone with 6 feet separation in between each of the users, ensuring that yellow and red always have a given distance barrier (e.g., 6 feet) between each of the users and/or between the groups of populations (e.g., a warning may be transmitted or provided to a physical space operator if such barrier is not possible), populating blue (e.g. users associated with low transmission risk) and/or blank seating (e.g., empty or buffer seats) to improve the given distance barrier (e.g., 6 feet) to separate red from the rest of the users. In embodiments, green individuals (e.g., users associated with moderate or medium transmission risk) may be used in place of blue where there is not enough blue population. In embodiments, empty seating may be used in place of green where there is not enough green population. In embodiments, blue individuals may be populated within a scattered yellow population. In embodiments, seating of blue individuals may be prioritized over seating green individuals, which may be prioritized over leaving seats empty, depending on capacity of the physical space.

In embodiments, allocating physical space assignments may prioritize separation of blue and green populations. In embodiments, allocating physical space assignments may prioritize equal mixing of blue and green populations. In embodiments, allocating physical space assignments may prioritize “thickening” a physical distance barrier with a remainder of blue population individuals (e.g., if there is enough blue population to generate 2 rows of blue as barrier instead of 1 row, prioritize this).

In embodiments, allocating physical space assignments may be performed iteratively until red individuals are barricaded by blue and/or blank or empty seating, yellow population individuals are barricaded by blue, and then the remaining population is seated. If any of the aforementioned rules are preferred and cannot be satisfied, an exception may be thrown (e.g., a notification may be transmitted or provided) to the operator of the physical space and/or manual adjustment of seating may be performed.

In embodiments, allocating physical space assignments may be based at least in part on a risk ceiling associated with the physical space. A risk ceiling may be defined according to criteria set by an operator of the physical space. For example, a risk ceiling may be defined based in part on based at least in part on potential collision (e.g., how likely will red collide with yellow, or red collide with green, where a collision event may be defined as red within a certain proximity of yellow (or other transfer risk score grouping) over a certain period).

In embodiments, a risk ceiling may be defined based at least in part on a makeup of the population (e.g., how many red, yellow, green, and blue individuals) to be included within the physical space.

The risk ceiling provides a mechanism by which a safety threshold may be applied to a physical space. For example, a given area (e.g., a room within a physical space) might only have room for 1 more red; a given area may need more blue individuals; a given area may need an empty seat since there may not be enough blue individuals; and the like. Further, blue individuals may be incentivized by the operator of the physical space to move to a different time slot.

For example, a user may be reassigned to a different physical space assignment to minimize risk overall. By way of further example, a user may be "nudged" to pick a certain time based at least in part on minimizing risk overall (e.g., the price may be lower or higher based at least in part on the transfer risk score grouping associated with the user and/or the rest of the users already assigned within the physical space). In certain embodiments, changes in a transfer risk score or transfer risk score grouping (e.g., based at least in part on updates in immunization, willingness to wear PPE, updates from the FDA, a positive or negative test (e.g., COVID-19), contraindication with a given vaccine, delay in vaccination information update to a data repository) may lead to adjusting physical space assignments.

In FIG. 14B, an apparatus (e.g., such as viral transfer risk management computing entity 106) may be configured to retrieve 1404 a plurality of nearby user identifiers each associated with a different nearby client computing entity of a plurality of nearby client computing entities (e.g., such as client computing entity 102) within a first proximity of the first client computing entity. The apparatus may be further configured to, for each nearby user identifier of the plurality of nearby user identifiers, determine 1405, based at least in part on a respective transfer risk score associated with the nearby user identifier, a respective transfer risk score grouping. The apparatus may be further configured to, upon detecting 1406 a change in location associated with the first client computing entity, based at least in part on the physical space parameters, locations associated with the plurality of nearby client computing entities, and the respective transfer risk score groupings associated with the plurality of nearby user identifiers, transmit 1407 a collision potential notification to the first client computing entity.

In embodiments, labels (e.g., colors) may be associated with transfer risk score groupings. The dynamically defined risk thresholds may be configurable for a given physical space identifier and/or adjusted according to changes in transmissibility risk information and/or government regulations. In examples, transfer risk score groupings may be one of low, moderate, high, or waiver exception. In examples, a low transfer risk grouping may be associated with a transfer risk score of less than 10%, a moderate transfer risk grouping may be associated with a transfer risk score of at least 10% and less than 80%, a high transfer risk grouping may be associated with a transfer score of at least 80%, and a waiver exception transfer risk grouping may be associated with a transfer risk record having a transfer risk record value representing a waiver exception to having been immunized. A waiver exception may be based at least in part on a medical condition and/or a self-declared election to opt out of immunization. Embodiments herein may refer to the various transfer risk score groupings according to colors (e.g., blue, red, green, yellow) or other relative terms (e.g., low, moderate or medium, high, waiver/exception) for the purposes of illustration and not for the purposes of limiting transfer risk score groupings to the definitions presented herein. In embodiments, regulatory-based logic may be used to assign transfer risk score groupings or labels (e.g., if some states require a higher TR % to operate, it will be reflected in the transfer risk score groupings).

Figure 14C:
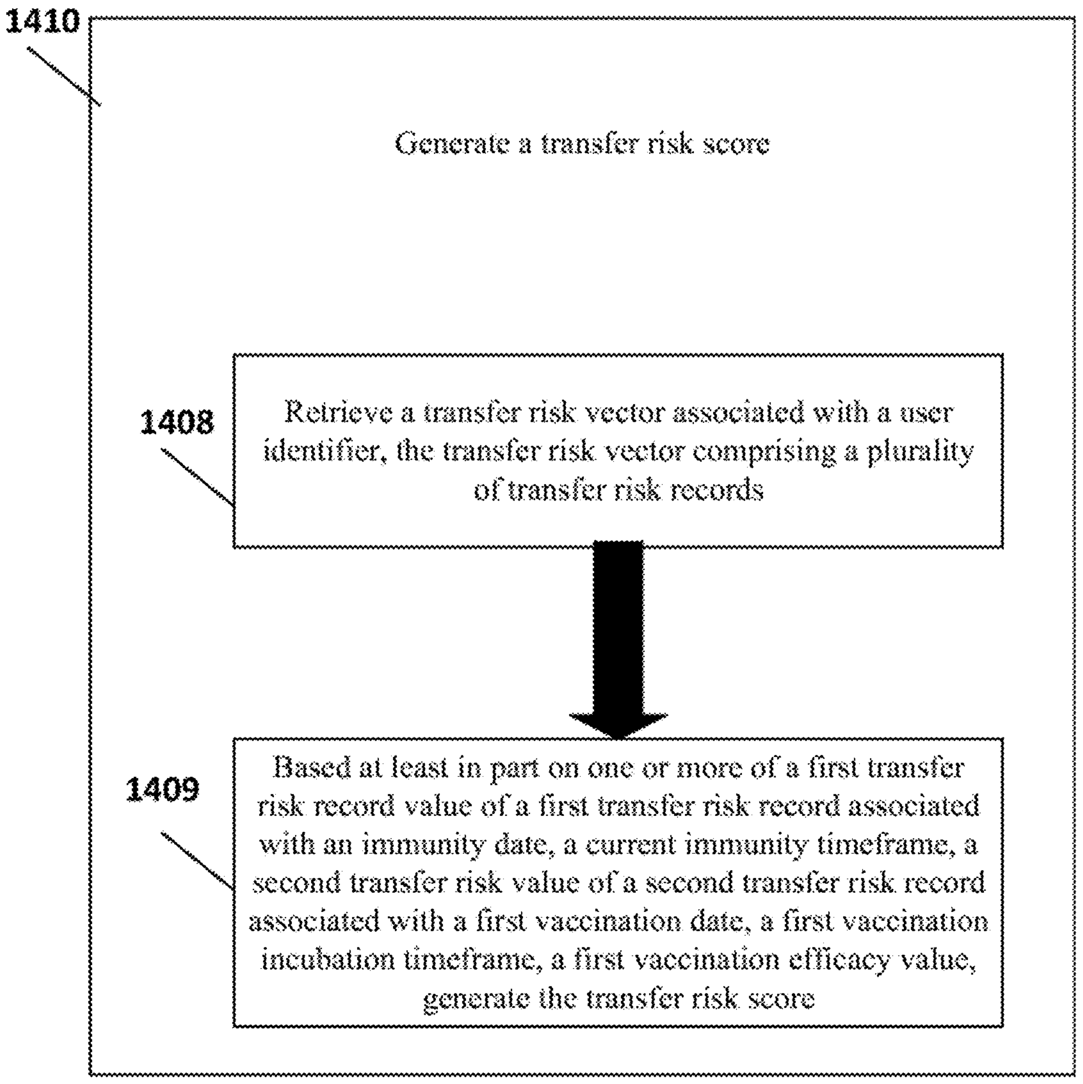

In FIG. 14C, an apparatus (e.g., such as viral transfer risk management computing entity 106) may be configured to generate 1410 a transfer risk score by retrieving 1408 a transfer risk vector associated with a user identifier, the transfer risk vector comprising a plurality of transfer risk records. The apparatus may be further configured to, based at least in part on one or more of a first transfer risk record value of a first transfer risk record associated with an immunity date, a current immunity timeframe, a second transfer risk value of a second transfer risk record associated with a first vaccination date, a first vaccination incubation timeframe, a first vaccination efficacy value, generate 1409 the transfer risk score.

In embodiments, transfer risk scores may be generated based in part on an immunity lifecycle calculation (e.g., if the CDC declares that immunity lasts for 30 days, then changes it to 180 days, the immunity lifecycle calculation will be automatically updated and scores and groupings will reflect the update). In embodiments, transfer risk scores may be generated based in part on a conflicting vaccination detection (e.g., if it is not recommended to take vaccine A and then vaccine B within 90 days, the transfer risk score and grouping will reflect the conflict). In embodiments, transfer risk scores may be generated based in part on an off label vaccination (e.g., a user may declare an off label vaccination; e.g., emergency use authorization, or non-FDA approved vaccination). In embodiments, transfer risk scores may be generated based in part on an effectiveness or vaccination of a vaccine (e.g., if studies of vaccine(s) determine that an emergency use authorization is not as effective as a newer vaccine, or if a vaccine is associated with an expiration date, transfer risk scores and groupings will reflect this adjustment).

In embodiments, a user may present information representing a transfer risk score, a transfer risk score grouping (e.g., a label or a color), and/or a transfer risk vector associated with the user upon entry to a physical space (or upon request from an entity associated with the physical space).

In embodiments, the physical space may be equipped with one or more sensors configured to determine or read a position from a client computing entity (e.g., phone or IOT device). In embodiments, a wireless access point may be used for triangulation to determine positions or locations. In embodiments, an array of sensors may be used to determine positions or locations. In embodiments, a client computing entity associated with a user may be pre-loaded with a physical space assignment for the user and/or information representing a transfer risk score, a transfer risk score grouping (e.g., a label or a color), and/or a transfer risk vector associated with the user. The client computing entity may also receive instructions for displaying a transfer risk map (e.g., this may guide the user to move to their assigned seating). In embodiments, if it is detected that a user violates their assigned position, a warning may be issued to the user (e.g., the client computing entity associated with the user) as well as a computing entity associated with the operator of the physical space.

In embodiments, once a user is in their assigned position, the client computing entity associated with the user may be configured to activate a viral load collision mode. In such a mode, a user may be warned (e.g., by way of notification) depending on their immunity status whether they are moving in or toward a location that is risky (e.g., where transfer or transmission risk may be high for the user).

In embodiments, a user associated with a high transmission risk transfer risk score grouping (e.g., red) that may venture outside of a barricade associated therewith (e.g., outside of ae blue barricade), a warning may be issued to the user (e.g., the client computing entity associated with the user) as well as a computing entity associated with the operator of the physical space.

In embodiments, a user associated with a waiver/exception grouping (e.g., yellow) may be warned (e.g., by way of notification to a client computing entity associated with the user) if the user is about to enter a particular radius (e.g., 3 feet radius) of another yellow, green, or red individual.

In embodiments, a user associated with a moderate grouping (e.g., green) may be warned (e.g., by way of notification to a client computing entity associated with the user) if the user is about to enter a particular radius (e.g., 3 feet radius) of red.

In embodiments, a user associated with a low grouping (e.g., blue) may be warned (e.g., by way of notification to a client computing entity associated with the user) if the user wanders too far from their expected or assigned location.

In embodiments, the collision detection may be overridden based at least in part on temporary movement (e.g., to the rest room). In such embodiments, if a user is detected as moving away from their assigned location, a timer may start such that if the user returns to their assigned location within this t1 window, no action is taken. However, if the user does not return within this t1 window, a warning may be issued to the user (e.g., the client computing entity associated with the user) as well as a computing entity associated with the operator of the physical space.

In embodiments, whenever there is a collision, a warning may be issued to the user (e.g., the client computing entity associated with the user) as well as a computing entity associated with the operator of the physical space. Further, a map may be displayed (e.g., and updated with movement and collision history). In embodiments, the warnings include recommended actions to correct the collisions. In embodiments, a collision factor may be assigned to the collision, where the collision factor may depend on regulatory and/or scientific information. For example, if an individual comes within a given distance (e.g., 6 feet radius) of a red individual, a collision factor for the individual may be increased at rate of 1 viral load/minutes. Collisions may be summed up for any given client computing entity and, if the collision factor is higher than a defined threshold, a corrective action may be triggered (e.g., a notification may be sent to the client computing entity with recommended actions or movements).

Figure 14D:
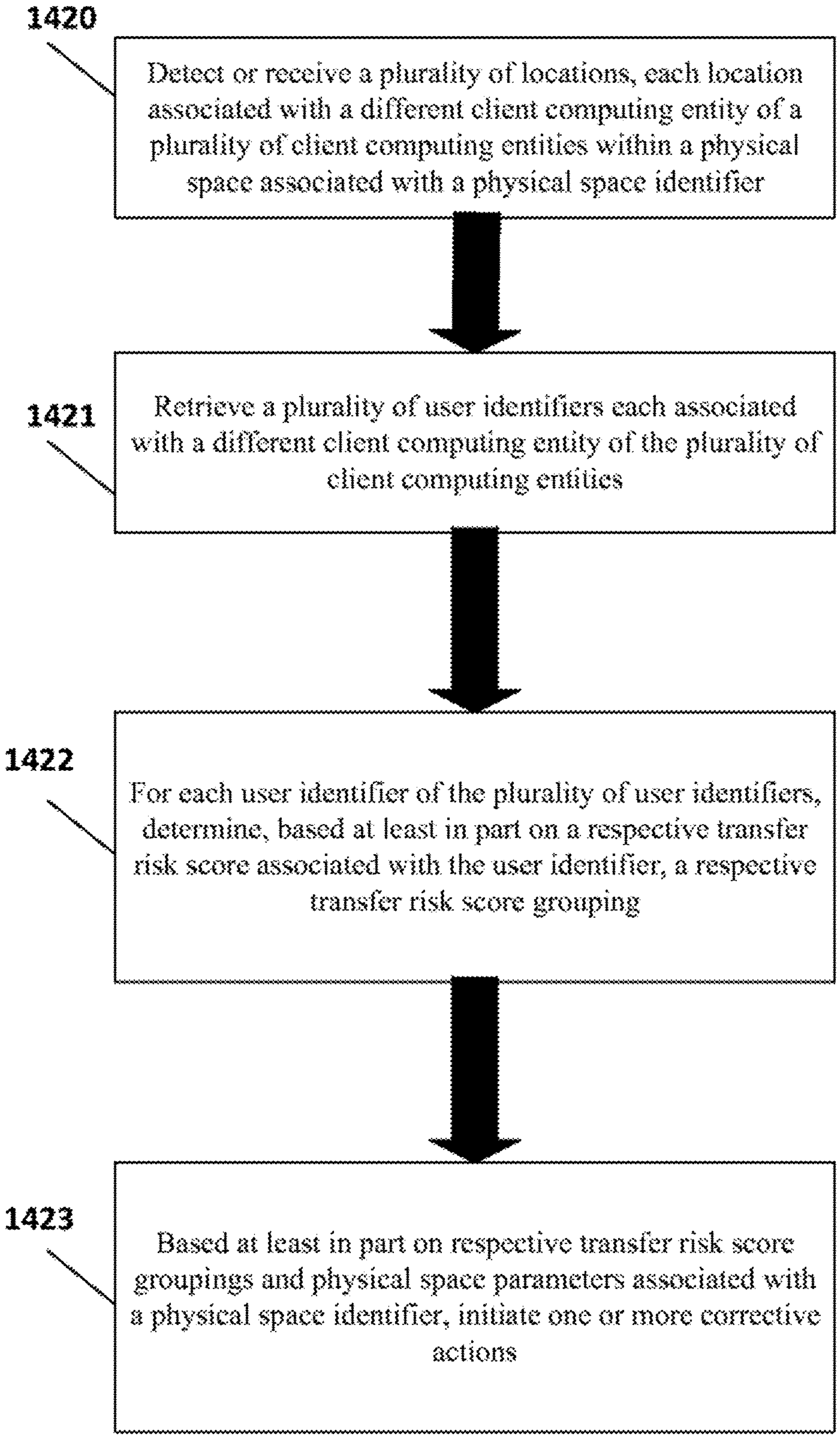

In FIG. 14D, an apparatus (e.g., such as viral transfer risk management computing entity 106) may be configured to detect or receive 1420 a plurality of locations, each location associated with a different client computing entity of a plurality of client computing entities within a physical space associated with a physical space identifier. The apparatus may be further configured to retrieve 1421 a plurality of user identifiers each associated with a different client computing entity of the plurality of client computing entities. The apparatus may be further configured to, for each user identifier of the plurality of user identifiers, determine 1422, based at least in part on a respective transfer risk score associated with the user identifier, a respective transfer risk score grouping. The apparatus may be further configured to, based at least in part on respective transfer risk score groupings and physical space parameters associated with a physical space identifier, initiate 1423 one or more corrective actions.

In embodiments, the physical space is equipped with various viral input sensors. Non-limiting examples of sensors include a particle counter, a camera, a microphone, a thermal camera, a client computing entity configured to detect viral transmission risk statements based at least in part on speech detection and natural language processing, or regression-based sensors configured to detect changes in skin color.

Table 1 illustrates examples of corrective actions. Table 2 illustrates examples of notifications or information that may be provided to a user (e.g., via a client computing entity associated with the user). FIG. 15 illustrates an example collision report interface in accordance with some embodiments of the present disclosure.

TABLE 1

Corrective Actions

| Category | Possible Actions |
|---|---|
| Mobile Filtration | HEPA filter fan mounted on path aware mobile station (e.g., Roomba, drones) |
| Mobile Sanitization | UV light on mobile station<br>Automated anti-bacterial spray |
| Exhaust Redirection | Zone control HVAC<br>Windows open/close |
| User Alert/Notification | Alert and direct user to a certain location<br>Vaccination booster shot and/or prophylactic actions |

TABLE 2

Metrics for Notifications

| Category | Relevant Metrics |
|---|---|
| Viral Input | Two people cough/sneeze within 6 feet<br>Particle count was higher than threshold for 15 minutes<br>Three people have high body temperature |
| Collision Calculation | You have been exposed to 30 person-minutes of high transfer risk population |
| Corrective Action | Due to a cough/sneeze event, air flow was increased from X to Y cubic feet/meter<br>A mobile HEPA filter was sent to the site within Z minutes |
| Proposed Medical Conversation | Vaccination booster shot<br>Medical preventative (prophylactic actions)<br>Here is your contact tracing history |

In various embodiments, an apparatus for viral transfer risk management includes at least one processor and at least one non-transitory storage medium storing instructions that, with the at least one processor, configure the apparatus to retrieve a first user identifier associated with a first client computing entity. In some of these embodiments, the apparatus is further configured to determine, based at least in part on a first transfer risk score associated with the first user identifier, a first transfer risk score grouping for the first user identifier. In some of these embodiments, the apparatus is further configured to, based at least in part on the first transfer risk score grouping, and physical space parameters associated with a physical space identifier, allocate a first physical space assignment within a physical space associated with the physical space identifier to the first user identifier associated with the first client computing entity.

In some of these embodiments, physical space parameters comprise one or more of physical space shape, physical space square footage, physical space restricted areas, physical space openings, physical space ventilation pattern, physical space ventilation capabilities, available physical space assignments, or reserved physical space assignments. In some of these embodiments, each reserved physical space assignment is associated with a respective transfer risk score associated with a respective user identifier to which the reserved physical space assignment is allocated. In some of these embodiments, allocating the first physical space assignment to the first user identifier is further based, at least in part, on transfer risk groupings associated with respective user identifiers associated with reserved physical space assignments.

In some of these embodiments, the apparatus is further configured to retrieve a plurality of nearby user identifiers each associated with a different nearby client computing entity of a plurality of nearby client computing entities within a first proximity of the first client computing entity. In some of these embodiments, the apparatus is further configured to, for each nearby user identifier of the plurality of nearby user identifiers, determine, based at least in part on a respective transfer risk score associated with the nearby user identifier, a respective transfer risk score grouping. In some of these embodiments, the apparatus is further configured to, upon detecting a change in location associated with the first client computing entity, based at least in part on the physical space parameters, locations associated with the plurality of nearby client computing entities, and the respective transfer risk score groupings associated with the plurality of nearby user identifiers, transmit a collision potential notification to the first client computing entity.

In some of these embodiments, allocating the first physical space assignment within the physical space associated with the physical space identifier to the first user identifier is based at least in part on minimizing viral transmission risk for one or more client computing entities of a plurality of client computing entities within the physical space.

In some of these embodiments, a transfer risk grouping is one of low, moderate, high, or waiver exception. In some of these embodiments, allocating the first physical space assignment is based at least in part on distributing physical space assignments such that client computing entities associated with low transfer risk groupings are positioned closest to a physical space ventilation pattern starting point and client computing entities associated with high transfer risk groupings are positioned closest to a physical space ventilation pattern end point. In some of these embodiments, allocating the first physical space assignment is further based at least in part on distributing physical space assignments such that client computing entities associated with moderate transfer risk groupings are positioned between those client computing entities associated with high transfer risk groupings and low transfer risk groupings.

In some of these embodiments, allocating the first physical space assignment is further based at least in part on distributing physical space assignments such that client computing entities associated with waiver exception transfer risk groupings are positioned among those client computing entities associated with low transfer risk groupings and at least a required physical distance away from those client computing entities associated with high transfer risk groupings.

In some of these embodiments, a low transfer risk grouping is associated with a transfer risk score of less than 10%, a moderate transfer risk grouping is associated with a transfer risk score of at least 10% and less than 80%, a high transfer risk grouping is associated with a transfer score of at least 80%, and a waiver exception transfer risk grouping is associated with a transfer risk record having a transfer risk record value representing a waiver exception to having been immunized. In some of these embodiments, the transfer risk groupings are assigned based at least in part on one or more of physical space capacities or regulatory or scientific thresholds.

In some of these embodiments, the apparatus is further configured to generate the first transfer risk score by retrieving a first transfer risk vector associated with the first user identifier, the first transfer risk vector comprising a plurality of transfer risk records, and, based at least in part on one or more of a first transfer risk record value of a first transfer risk record associated with an immunity date, a current immunity timeframe, a second transfer risk value of a second transfer risk record associated with a first vaccination date, a first vaccination incubation timeframe, a first vaccination efficacy value, generating the first transfer risk score. In some of these embodiments, other transfer risk records of the plurality of transfer risk records comprise one or more of transfer risk record values representative of one or more vaccination records, personal protective equipment (PPE) wearing habits, natural immunity, immunization declaration, one or more medical conditions, or medical history.

In some of these embodiments, the apparatus is further configured to store a distributed ledger record associated with the first user identifier in a distributed ledger.

In some of these embodiments, the apparatus is further configured to generate a public-private key pair associated with the first user identifier. In some of these embodiments, the apparatus is further configured to, upon receipt, originating from the first client computing entity, of the private key associated with the first user identifier, retrieve a distributed ledger record associated with the first user identifier from a distributed ledger, decrypt the distributed ledger record using the private key, and transmit, to the client computing entity, a transfer risk transcript interface configured for display via the client computing entity.

In some of these embodiments, transmitting the collision potential notification is further based at least in part on a detected velocity or position with respect to time and its derivatives associated with the first client computing entity and a safe physical distance threshold associated with the first transfer risk score grouping associated with the first user identifier.

In some of these embodiments, the collision potential notification comprises one or more corrective movement recommendations.

In some of these embodiments, the physical space comprises an airplane, a restaurant, a vehicle, a multi-passenger vehicle, or a venue.

In some of these embodiments, the proximity is based at least in part on regulatory and scientific information and known transmissibility risks.

In some of these embodiments, allocating the first physical space assignment to the first user identifier is further based at least in part on a risk ceiling associated with the physical space associated with the physical space identifier, and wherein the risk ceiling is generated based at least in part on a configurable safety threshold defined for the physical space.

In some of these embodiments, the apparatus is further configured to detect a location associated with the first client computing entity, and, upon determining the first client computing entity is within the physical space associated with the physical space identifier and that the first client computing entity is associated with the first physical space assignment, transmit a physical space assignment interface to the first client computing entity for display via the first client computing entity.

In various embodiments, a computer program product for viral transfer risk management includes at least one non-transitory storage medium storing instructions that, with at least one processor, configure an apparatus to retrieve a first user identifier associated with a first client computing entity. In some of these embodiments, the apparatus is further configured to determine, based at least in part on a first transfer risk score associated with the first user identifier, a first transfer risk score grouping for the first user identifier. In some of these embodiments, the apparatus is further configured to, based at least in part on the first transfer risk score grouping, and physical space parameters associated with a physical space identifier, allocate a first physical space assignment within a physical space associated with the physical space identifier to the first user identifier associated with the first client computing entity.

In various embodiments, a computer implemented method for viral transfer risk management includes retrieving a first user identifier associated with a first client computing entity. In some of these embodiments, the method further includes determining, based at least in part on a first transfer risk score associated with the first user identifier, a first transfer risk score grouping for the first user identifier. In some of these embodiments, the method further includes, based at least in part on the first transfer risk score grouping, and physical space parameters associated with a physical space identifier, allocating a first physical space assignment within a physical space associated with the physical space identifier to the first user identifier associated with the first client computing entity.

In various embodiments, an apparatus for viral transfer risk management includes at least one processor and at least one non-transitory storage medium storing instructions that, with the at least one processor, configure the apparatus to detect or receive a plurality of locations, each location associated with a different client computing entity of a plurality of client computing entities within a physical space associated with a physical space identifier. In some of these embodiments, the apparatus is further configured to retrieve a plurality of user identifiers each associated with a different client computing entity of the plurality of client computing entities. In some of these embodiments, the apparatus is further configured to, for each user identifier of the plurality of user identifiers, determine, based at least in part on a respective transfer risk score associated with the user identifier, a respective transfer risk score grouping. In some of these embodiments, the apparatus is further configured to, based at least in part on respective transfer risk score groupings and physical space parameters associated with a physical space identifier, initiate one or more corrective actions.

In some of these embodiments, physical space parameters comprise one or more of physical space shape, physical space height, physical space square footage, physical space restricted areas, physical space openings, physical space ventilation pattern, physical space ventilation capabilities, available physical space assignments, or reserved physical space assignments.

In some of these embodiments, initiating a corrective action comprises one or more of adjusting air filtration associated with the physical space, adjusting sanitation associated with the physical space, adjusting exhaust associated with the physical space, or transmitting a collision potential notification to one or more client computing entities of the plurality of client computing entities. In some of these embodiments, adjusting air filtration associated with the physical space comprises controlling a HEPA filter fan. In some of these embodiments, adjusting sanitation associated with the physical space comprises one or more of activating one or more UV light stations within the physical space or activating one or more anti-bacterial spray stations within the physical space. In some of these embodiments, adjusting exhaust associated with the physical space comprises one or more of exhaust redirection, HVAC zone control adjustments, or automatic window adjustments.

In some of these embodiments, the collision potential notification comprises one or more corrective movement recommendations.

In some of these embodiments, initiating the one or more corrective actions is based at least in part on minimizing viral transmission risk for one or more client computing entities of a plurality of client computing entities within the physical space.

In some of these embodiments, detecting the plurality of locations is based at least in part on signals received from one or more sensors within the physical space.

In some of these embodiments, the one or more sensors comprise one or more of a particle counter, a camera, a microphone, a thermal camera, a client computing entity configured to detect viral transmission risk statements based at least in part on speech detection and natural language processing, or regression-based sensors configured to detect changes in skin color.

In some of these embodiments, the apparatus is further configured to initiate one or more corrective actions based upon detection of a viral load increase, wherein detection of a viral load increase is based at least in part on one or more of detection of a sneeze, detection of a particle count above a particle count threshold, or detection of one or more body temperatures above a body temperature threshold.

In some of these embodiments, the apparatus is further configured to generate and transmit, to a first client computing entity of the plurality of client computing entities, a collision report interface configured for display via the first client computing entity. In some of these embodiments, the collision report interface comprises graphical representations of one or more of accumulated viral input and collision calculations, corrective actions that were initiated during a time window within which the first client computing entity was within the physical space, or proposed medical actions to be performed in accordance with a first user identifier associated with the first client computing entity.

In some of these embodiments, the apparatus is further configured to generate the respective transfer risk score for each user identifier of the plurality of user identifiers by retrieving a transfer risk vector associated with the user identifier, the transfer risk vector comprising a plurality of transfer risk records, and based at least in part on one or more of a first transfer risk record value of a first transfer risk record associated with an immunity date, a current immunity timeframe, a second transfer risk value of a second transfer risk record associated with a first vaccination date, a first vaccination incubation timeframe, a first vaccination efficacy value, a first vaccination expiration date, generating the respective transfer risk score.

In some of these embodiments, other transfer risk records of the plurality of transfer risk records comprise one or more of transfer risk record values representative of one or more vaccination records, personal protective equipment (PPE) wearing habits, natural immunity, immunization declaration, one or more medical conditions, or medical history.

In some of these embodiments, a transfer risk grouping is one of low, moderate, high, or waiver exception. In some of these embodiments, a low transfer risk grouping is associated with a transfer risk score of less than 10%, a moderate transfer risk grouping is associated with a transfer risk score of at least 10% and less than 80%, a high transfer risk grouping is associated with a transfer score of at least 80%, and a waiver exception transfer risk grouping is associated with a transfer risk record having a transfer risk record value representing a waiver exception to having been immunized.

In some of these embodiments, the transfer risk groupings are assigned based at least in part on one or more of physical space capacities or scientific or regulatory thresholds.

In various embodiments, a computer program product for viral transfer risk management includes at least one non-transitory storage medium storing instructions that, with at least one processor, configure an apparatus to detect or receive a plurality of locations, each location associated with a different client computing entity of a plurality of client computing entities within a physical space associated with a physical space identifier. In some of these embodiments, the apparatus is further configured to retrieve a plurality of user identifiers each associated with a different client computing entity of the plurality of client computing entities. In some of these embodiments, the apparatus is further configured to, for each user identifier of the plurality of user identifiers, determine, based at least in part on a respective transfer risk score associated with the user identifier, a respective transfer risk score grouping. In some of these embodiments, the apparatus is further configured to, based at least in part on respective transfer risk score groupings and physical space parameters associated with a physical space identifier, initiate one or more corrective actions.

In various embodiments, a computer-implemented method for viral transfer risk management includes detecting or receiving a plurality of locations, each location associated with a different client computing entity of a plurality of client computing entities within a physical space associated with a physical space identifier. In some of these embodiments, the method further includes retrieving a plurality of user identifiers each associated with a different client computing entity of the plurality of client computing entities. In some of these embodiments, the method further includes, for each user identifier of the plurality of user identifiers, determining, based at least in part on a respective transfer risk score associated with the user identifier, a respective transfer risk score grouping. In some of these embodiments, the method further includes, based at least in part on respective transfer risk score groupings and physical space parameters associated with a physical space identifier, initiate one or more corrective actions.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system comprising one or more processors and at least one memory storing processor-executable instructions that, when executed by the one or more processors, cause the one or more processors to perform operations comprising:

receiving a first user identifier associated with a first client computing entity;

determining, based at least in part on (i) a first transfer risk score associated with the first user identifier, (ii) real-time updates to respective transfer risk scores associated with a plurality of nearby user identifiers, and (iii) an adjustable risk threshold associated with one or more government regulations, a first transfer risk score grouping for the first user identifier;

detecting speech that is spoken within a physical space associated with a physical space identifier;

determining, based at least in part on applying speech detection and natural language processing to the speech, one or more viral transmission risk statements within the speech;

based at least in part on the first transfer risk score grouping, one or more physical space parameters associated with the physical space identifier, and the one or more viral transmission risk statements, controlling an HVAC system within a physical space associated with the physical space identifier by adjusting air filtration associated with the physical space or adjusting exhaust associated with the physical space; and allocating a first physical space assignment based at least in part on distributing physical space assignments such that client computing entities associated with low transfer risk groupings are positioned closest to a physical space ventilation pattern starting point and client computing entities associated with high transfer risk groupings are positioned closest to a physical space ventilation pattern end point and such that client computing entities associated with moderate transfer risk groupings are positioned between those client computing entities associated with high transfer risk groupings and low transfer risk groupings.

2. The system of claim 1, wherein the one or more physical space parameters comprise one or more of physical space shape, physical space height, physical space square footage, physical space restricted areas, physical space openings, physical space ventilation pattern, physical space ventilation capabilities, available physical space assignments, or reserved physical space assignments.

3. The system of claim 2, wherein a reserved physical space assignment of the reserved physical space assignments is associated with a respective transfer risk score associated with a respective user identifier to which the reserved physical space assignment is allocated.

4. The system of claim 1, wherein the operations further comprise:

receiving the plurality of nearby user identifiers each associated with a different nearby client computing entity of a plurality of nearby client computing entities within a first proximity of the first client computing entity;

for each nearby user identifier of the plurality of nearby user identifiers, determining, based at least in part on a respective transfer risk score associated with the nearby user identifier, a respective transfer risk score grouping; and responsive to detecting a change in location associated with the first client computing entity, based at least in part on the one or more physical space parameters, locations associated with the plurality of nearby client computing entities, and respective transfer risk score groupings associated with the plurality of nearby user identifiers, transmitting a collision potential notification to the first client computing entity.

5. The system of claim 1, further comprising:

one or more of adjusting sanitation associated with the physical space or allocating a first physical space assignment to the first user identifier based at least in part on transfer risk groupings associated with other user identifiers associated with reserved physical space assignments and minimizing viral transmission risk for one or more client computing entities of a plurality of client computing entities within the physical space.

6. The system of claim 1, wherein the first transfer risk score grouping is one of low, moderate, high, or waiver exception.

7. The system of claim 1, wherein allocating the first physical space assignment is further based at least in part on distributing physical space assignments such that client computing entities associated with waiver exception transfer risk groupings are positioned among those client computing entities associated with low transfer risk groupings and at least a required physical distance away from those client computing entities associated with high transfer risk groupings.

8. The system of claim 6, wherein a low transfer risk grouping is associated with a transfer risk score of less than 10%, a moderate transfer risk grouping is associated with a transfer risk score of at least 10% and less than 80%, a high transfer risk grouping is associated with a transfer score of at least 80%, and a waiver exception transfer risk grouping is associated with a transfer risk record having a transfer risk record value representing a waiver exception to having been immunized.

9. The system of claim 6, wherein the adjustable risk threshold is further associated with one or more physical space capacities.

10. The system of claim 1, wherein the operations further comprise generating the first transfer risk score by:

retrieving a first transfer risk vector associated with the first user identifier, the first transfer risk vector comprising a plurality of transfer risk records; and based at least in part on one or more of a first transfer risk record value of a first transfer risk record associated with an immunity date, a current immunity timeframe, a second transfer risk value of a second transfer risk record associated with a first vaccination date, a first vaccination incubation timeframe, a first vaccination efficacy value, generating the first transfer risk score.

11. The system of claim 10, wherein other transfer risk records of the plurality of transfer risk records comprise one or more of transfer risk record values representative of one or more vaccination records, personal protective equipment (PPE) wearing habits, natural immunity, immunization declaration, one or more medical conditions, or medical history.

12. The system of claim 1, wherein the operations further comprise:

storing a distributed ledger record associated with the first user identifier in a distributed ledger.

13. The system of claim 1, wherein the operations further comprise:

transmitting control signals to the HVAC system.

14. The system of claim 12, wherein the operations further comprise:

responsive to receiving, originating from the first client computing entity, a private key of a public-private key pair associated with the first user identifier, receiving a distributed ledger record associated with the first user identifier from a distributed ledger;

decrypting the distributed ledger record using the private key; and transmitting, to the first client computing entity, a transfer risk transcript interface configured for display via the first client computing entity.

15. The system of claim 4, wherein transmitting the collision potential notification is further based at least in part on a detected velocity or position with respect to time and its derivatives associated with the first client computing entity and a safe physical distance threshold associated with the first transfer risk score grouping associated with the first user identifier.

16. The system of claim 4, wherein the collision potential notification comprises one or more corrective movement recommendations.

17. The system of claim 1, wherein the physical space comprises an airplane, a restaurant, a vehicle, a multi-passenger vehicle, or a venue.

18. The system of claim 4, wherein the first proximity is based at least in part on regulatory and scientific information and known transmissibility risks.

19. The system of claim 1, wherein the operations further comprise:

allocating a first physical space assignment to the first user identifier based at least in part on a risk ceiling associated with the physical space associated with the physical space identifier, and wherein the risk ceiling is generated based at least in part on a configurable safety threshold defined for the physical space.

20. The system of claim 1, wherein the operations further comprise:

detecting a location associated with the first client computing entity; and responsive to determining the first client computing entity is within the physical space associated with the physical space identifier and that the first client computing entity is associated with a first physical space assignment, transmitting a physical space assignment interface to the first client computing entity for display via the first client computing entity.

21. One or more non-transitory computer-readable storage media including instructions that, when executed by one or more processors, cause the one or more processors to perform operations comprising:

receiving a first user identifier associated with a first client computing entity;

determining, based at least in part on (i) a first transfer risk score associated with the first user identifier, (ii) real-time updates to respective transfer risk scores associated with a plurality of nearby user identifiers, and (iii) an adjustable risk threshold associated with one or more government regulations, a first transfer risk score grouping for the first user identifier;

detecting speech that is spoken within a physical space associated with a physical space identifier;

determining, based at least in part on applying speech detection and natural language processing to the speech, one or more viral transmission risk statements within the speech;

based at least in part on the first transfer risk score grouping, one or more physical space parameters associated with the physical space identifier, and the one or more viral transmission risk statements, controlling an HVAC system within a physical space associated with the physical space identifier by adjusting air filtration associated with the physical space or adjusting exhaust associated with the physical space; and allocating a first physical space assignment based at least in part on distributing physical space assignments such that client computing entities associated with low transfer risk groupings are positioned closest to a physical space ventilation pattern starting point and client computing entities associated with high transfer risk groupings are positioned closest to a physical space ventilation pattern end point and such that client computing entities associated with moderate transfer risk groupings are positioned between those client computing entities associated with high transfer risk groupings and low transfer risk groupings.

22. A computer-implemented method comprising:

receiving, by one or more processors, a first user identifier associated with a first client computing entity;

determining, by the one or more processors and based at least in part on (i) a first transfer risk score associated with the first user identifier, (ii) real-time updates to respective transfer risk scores associated with a plurality of nearby user identifiers, and (iii) an adjustable risk threshold associated with one or more government regulations, a first transfer risk score grouping for the first user identifier;

detecting speech that is spoken within a physical space associated with a physical space identifier;

determining, based at least in part on applying speech detection and natural language processing to the speech, one or more viral transmission risk statements within the speech;

based at least in part on the first transfer risk score grouping, one or more physical space parameters associated with the physical space identifier, and the one or more viral transmission risk statements, controlling an HVAC system within a physical space associated with the physical space identifier by adjusting air filtration associated with the physical space or adjusting exhaust associated with the physical space; and allocating a first physical space assignment based at least in part on distributing physical space assignments such that client computing entities associated with low transfer risk groupings are positioned closest to a physical space ventilation pattern starting point and client computing entities associated with high transfer risk groupings are positioned closest to a physical space ventilation pattern end point and such that client computing entities associated with moderate transfer risk groupings are positioned between those client computing entities associated with high transfer risk groupings and low transfer risk groupings.

23. The system of claim 1, wherein the operations further comprise:

receiving a plurality of locations, each location associated with a different client computing entity of a plurality of client computing entities within a physical space associated with a physical space identifier;

receiving a plurality of user identifiers each associated with a different client computing entity of the plurality of client computing entities; and for each user identifier of the plurality of user identifiers, determining, based at least in part on a respective transfer risk score associated with the user identifier, a respective transfer risk score grouping.

* * * * *